United States Patent
Ullman et al.

(10) Patent No.: US 6,406,913 B1
(45) Date of Patent: Jun. 18, 2002

(54) ASSAY METHOD UTILIZING INDUCED LUMINESCENCE

(75) Inventors: Edwin F. Ullman, Atherton; Hrair Kirakossian, San Jose; John S. Pease, Los Altos; Yuri Daniloff, Mountain View; Daniel B. Wagner, Sunnyvale, all of CA (US)

(73) Assignee: Dade Behring Marburg GmbH, Marburg (DE)

( * ) Notice: Subject to any disclaimer, the term of this patent is extended or adjusted under 35 U.S.C. 154(b) by 0 days.

(21) Appl. No.: 08/471,130

(22) Filed: Jun. 6, 1995

Related U.S. Application Data

(63) Continuation of application No. 07/704,569, filed on May 22, 1991, now abandoned.

(51) Int. Cl.[7] .......................... G01T 1/161; C09K 3/00; G01N 21/76; G01N 33/53

(52) U.S. Cl. ...................... 435/968; 250/361; 252/700; 422/52; 435/7; 435/968; 435/971; 435/973; 435/975; 522/6; 522/8; 522/11; 522/12

(58) Field of Search .................... 250/361; 252/700; 422/52; 435/7, 968, 971, 973, 975; 522/6, 8, 11, 12

(56) References Cited

U.S. PATENT DOCUMENTS

| | | | |
|---|---|---|---|
| 3,720,622 A | | 3/1973 | Bollyky .................... 252/188.3 |
| 3,996,345 A | * | 12/1976 | Ullman et al. ................. 424/12 |
| 4,174,384 A | * | 11/1979 | Ullman et al. .................. 424/8 |
| 4,199,559 A | * | 4/1980 | Ullman et al. .................. 424/8 |
| 4,220,450 A | * | 9/1980 | Maggio ........................ 23/230 |
| 4,233,402 A | * | 11/1980 | Maggio .......................... 435/7 |
| 4,261,968 A | * | 4/1981 | Ullman et al. .................. 424/8 |
| 4,275,149 A | | 6/1981 | Litman et al. |
| 4,277,437 A | * | 7/1981 | Maggio .......................... 422/6 |
| 4,299,916 A | * | 11/1981 | Litman et al. .................. 435/6 |
| 4,318,707 A | * | 3/1982 | Litman et al. ................. 23/230 |
| 4,380,580 A | * | 4/1983 | Boguslaski et al. ............. 435/7 |
| 4,383,031 A | * | 5/1983 | Boguslaski et al. ............. 435/7 |
| 4,568,649 A | | 2/1986 | Bertoglio-Matte |
| 4,788,142 A | | 11/1988 | Hosaka et al. |
| 4,959,182 A | | 9/1990 | Schaap |
| 4,978,614 A | | 12/1990 | Bronstein |
| 5,143,853 A | | 9/1992 | Walt |
| 5,254,477 A | | 10/1993 | Walt |
| 5,340,716 A | | 8/1994 | Ullman et al. |
| 5,516,636 A | | 5/1996 | McCapra |
| 5,556,758 A | * | 9/1996 | Allen ............................ 435/7 |
| 5,616,719 A | | 4/1997 | Davalian et al. |
| 5,618,732 A | | 4/1997 | Pease et al. |
| 5,709,994 A | | 1/1998 | Pease et al. |
| 5,716,855 A | | 2/1998 | Lerner et al. |

FOREIGN PATENT DOCUMENTS

| | | | | |
|---|---|---|---|---|
| AU | 517292 | | 7/1981 | |
| EP | 070685 | * | 7/1982 | .......... G01N/33/58 |
| EP | 070687 | * | 7/1982 | .......... G01N/33/58 |
| EP | 0 144 914 A2 | | 6/1985 | |
| EP | 0 229 943 A2 | | 7/1987 | |
| EP | 0 275 260 B1 | | 7/1988 | |
| EP | 315364 | * | 10/1988 | .......... G01N/33/58 |
| EP | 0 315 364 A2 | | 5/1989 | |
| EP | 345776 | * | 6/1989 | .......... G01N/33/58 |
| EP | 0 345 776 A2 | | 12/1989 | |
| EP | 0 345 776 A3 | | 12/1989 | |
| EP | 0 352 713 B1 | | 1/1990 | |
| EP | 0 421 788 A2 | | 4/1991 | |
| EP | 476545 | * | 9/1991 | .......... G01N/33/542 |
| EP | 0 229 943 B1 | | 9/1991 | |
| EP | 0 476 545 A1 | | 3/1992 | |
| EP | 0 515 194 A2 | | 11/1992 | |
| WO | WO 88/00695 | | 1/1988 | |
| WO | WO 89/12232 | | 12/1989 | |
| WO | WO 90/02205 | | 3/1990 | |
| WO | WO 9103479 | * | 9/1990 | .............. C07F/9/06 |
| WO | WO 9403812 | * | 7/1993 | .......... G01N/33/58 |
| WO | WO 94/03812 | | 1/1994 | |
| WO | WO 95/06877 | | 3/1995 | |
| WO | WO 87/05334 | | 9/1997 | |

OTHER PUBLICATIONS

Seliger et al. 1982. Phtochem. Photobiol. 36:359–365. 1982.*

Turro et al. 1978. J. of Amer. Chem. Soc. 100(22): 7110–7112. 1978.*

Wang et al. 1976. J. Org. Chem. 41(16): 2685–2688. 1976.*

Heller et al., *Rapid Detection and Identification of Infectious Agents*, pp245–256, Chemiluminescent and Fluorescent Probes for DNA Hybridization Systems, 1985.

Lee et al., *J. of Organic Chem.* 41(16):2685–2688, "Chemiluminescence from the Reaction of Singlet Oxygen with 10, 10'–dimethyl–9,9'–biacridylidene. A Reactive 1,2–dioxetane", 1976.

Morrison et al., *Anal Biochem.*, 183:231–244, "Solution–Phase Detection of Polynucleotide Using Interacting Fluorescent Labels and Competitive Hybridization", 1989.

(List continued on next page.)

*Primary Examiner*—Lynette R. F. Smith
*Assistant Examiner*—Ja-Na Hines
(74) *Attorney, Agent, or Firm*—Finnegan, Henderson, Farabow, Garrett & Dunner L.L.P.

(57) ABSTRACT

Methods are disclosed for determining an analyte in a medium suspected of containing the analyte. One method comprises treating a medium suspected of containing an analyte under conditions such that the analyte, if present, causes a photosensitizer and a chemiluminescent compound to come into close proximity. The photosensitizer generates singlet oxygen and activates the chemiluminescent compound when it is in close proximity. The activated chemiluminescent compound subsequently produces light. The amount of light produced is related to the amount of analyte in the medium. Preferably, at least one of the photosensitizer and chemiluminescent compound is associated with a surface which is usually a suspendible particle, and a specific binding pair member is bound thereto. Compositions and kits are also disclosed.

93 Claims, 4 Drawing Sheets

OTHER PUBLICATIONS

Patel et al., *Anal. Biochem.* 129:162–169, "Chemiluminescence Energy Transfer: A new technique applicable to the study of ligand–ligand interactions n living systems", 1983.

Patel et al., *Biochemical Society Transactions* 11:196–197, "A homogeneous immunoassay method for cyclic AMP involving the use of chemiluminescence–energy transfer", 1983.

Seliger et al., *Photochem and Photobiol*, 36(3):359–365, "Chemiluminescence of benzo[a]pyrene–7,8–diol", 1982.

Turro et al., *J. Amer. Chem. Soc.*, 100(22):7110–7112, "Generation, Diffusivity, and Reactivity of Singlet Oxygen in Polymer Matrices. A Convenient and Sensitive Chemiluminescent Technique", Oct. 25, 1978.

Ullman et al., *Proc Natl Acad Sci.*, 91:5426–5430, "Luminescent Oxygen Channeling Assay: Measurement of Particle Binding Kinetics by Chemiluminescence", 1994.

Ullman et al., *Clin Chem.* 42(9):1518–1526, "Luminescent Oxygen Channeling Assay (LOCI™): Sensitive, Broadly Applicable Homogeneous Immunoassay Method", 1996.

Yemul et al., *Proc Natl Acad Sci.* 84:246–250, "Selective Killing of T–Lymphocytes by Phototoxic Liposomes", 1997.

* cited by examiner-

ASSAY METHOD UTILIZING INDUCED LUMINESCENCE

This is a continuation of application Ser. No. 07/704,569, filed May 22, 1991 now abandoned the disclosures of which are incorporated herein by reference.

BACKGROUND OF THE INVENTION

Field of the Invention

This invention relates to methods, compositions and kits for determining an analyte in a sample. In particular, this invention relates to specific binding assays which do not require a separation step.

The clinical diagnostic field has seen a broad expansion in recent years, both as to the variety of materials (analytes) that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

In developing an assay there are many considerations. One consideration is the signal response to changes in the concentration of analyte. A second consideration is the ease with which the protocol for the assay may be carried out. A third consideration is the variation in interference from sample to sample. Ease of preparation and purification of the reagents, availability of equipment, ease of automation and interaction with material of interest are some of the additional considerations in developing a useful assay.

One broad category of techniques involves the use of a receptor which can specifically bind to a particular spacial and polar organization of a labeled ligand as a function of the presence of an analyte. The observed effect of binding by the receptor will depend upon the label. In some instances the binding of the receptor merely provides for a differentiation in molecular weight between bound and unbound labeled ligand. In other instances the binding of the receptor will facilitate separation of bound labeled ligand from free labeled ligand or it may affect the nature of the signal obtained from the label so that the signal varies with the amount of receptor bound to labeled ligand. A further variation is that the receptor is labeled and the ligand unlabeled. Alternatively, both the receptor and ligand are labeled or different receptors are labeled with two different labels, whereupon the labels interact when in close proximity and the amount of ligand present affects the degree to which the labels of the receptor may interact.

There is a continuing need for new and accurate techniques that can be adapted for a wide spectrum of different ligands or be used in specific cases where other methods may not be readily adaptable.

Homogeneous immunoassays have previously been described for small molecules. These assays include SYVA's FRAT® assay, EMIT® assay, enzyme channeling immunoassay, and fluorescence energy transfer immunoassay (FETI); enzyme inhibitor immunoassays (Hoffman LaRoche and Abbott Laboratories): fluorescence polarization immunoassay (Dandlicker), among others. All of these methods have limited sensitivity, and only a few including FETI and enzyme channeling, are suitable for large multi-epitopic analytes.

Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as liposomes and erythrocyte ghosts, have been utilized as carriers of encapsulated water soluble materials. For example, liposomes have been employed to encapsulate biologically active material for a variety of uses, such as drug delivery systems wherein a medicament is entrapped during liposome preparation and then administered to the patient to be treated.

Particles, such as latex beads and liposomes, have also been utilized in assays. For example, in homogeneous assays an enzyme may be entrapped in the aqueous phase of a liposome labelled with an antibody or antigen. The liposomes are caused to release the enzyme in the presence of a sample and complement. Antibody- or antigen-labelled liposomes, having water soluble fluorescent or non-fluorescent dyes encapsulated within an aqueous phase or lipid soluble dyes dissolved in the lipid bilayer of the lipid vesicle, have also been utilized to assay for analytes capable of entering into an immunochemical reaction with the surface bound antibody or antigen. Detergents have been used to release the dyes from the aqueous phase of the liposomes.

2. Brief Description of the Related Art

European Patent Application No. 0,345,776 (McCapra) discloses specific binding assays that utilize a sensitizer as a label. The sensitizers include any moiety which, when stimulated by excitation with radiation of one or more wavelengths or other chemical or physical stimulus (e.g., electron transfer, electrolysis, electroluminescence or energy transfer) will achieve an excited state which (a) upon interaction with molecular oxygen will produce singlet molecular oxygen, or (b) upon interaction with a leuco dye will assume a reduced form that can be returned to its original unexcited state by interaction with molecular oxygen resulting in the production of hydrogen peroxide. Either interaction with the excited sensitizer will, with the addition of reagents, produce a detectible signal.

European Patent Application No. 0,070,685 (Heller, et al. I) describes a homogeneous nucleic acid hybridization diagnostic by non-radiative energy transfer.

A light-emitting polynucleotide hybridization diagnostic method is described in European Patent Application No. 0,070,687 (Heller, et al. II).

European Patent Application No. 0,232,967 (Morrison I) discusses methods and compositions for performing assays for target polynucleotide strands. The methods include contacting a sample with a reagent that includes a first and a second polynucleotide probe. The first and second probes are capable of assuming a first position wherein the probes are bound to each other and a second position wherein the probes are bound to a target. The probes include label moieties capable of interacting to produce a signal indicative of the probes being in one of the two positions.

European Patent Application No. 0,315,364 describes an immunochemical assay to determine the presence or concentration of antigen or antibodies in a fluid. The assay comprises (a) forming a ternary complex of a first labeled antibody or antigen, a second labeled antibody or antigen, and the antigen or antibody to be determined, and (b) detecting a signal produced in the presence of at least one substrate, by an interaction between the first label and the second label, enhanced by their proximity to each other bound to the antigenic substance.

European Patent Application No. 0,229,943 (Heller, et al. III) describes fluorescent Stokes shift probes for polynucleotide hybridization assays.

U.S. Pat. No. 4,226,993 (Buckler, et al.) describes immuno-functionalized phthalhydrazides, which are useful as intermediates in the synthesis of chemiluminescent phthalhydrazide-labeled conjugates. The conjugates are useful as reagents in specific binding assays for determining ligands or their specific binding partners in liquid media.

U.S. Pat. Nos. 4,380,580 and 4,383,031 (Boguslaski, et al. I and Boguslaski, et al. II) respectively describe heterogeneous and homogeneous chemiluminescent specific binding assays.

U.S. Pat. No. 4,220,450 (Maggio I) discusses chemically induced fluorescence immunoassays.

U.S. Pat. No. 4,652,533 (Jolley) describes a method of solid phase immunoassay incorporating a luminescent label.

U.S. Pat. No. 4,277,437 (Maggio II) discloses kits for carrying out chemically induced fluorescence immunoassays.

Heller, et al. (IV), describe chemiluminescent and fluorescent probes for DNA hybridization systems in "Rapid Detection and Identification of Infectious Agents" (1985) Academic Press, Inc., pages 245–257. Hara, et al., describe an immunoassay using a metal-complex compound as a chemiluminescent catalyst in *Bull. Chem. Soc. Jpn.* (1984) 57:3009–3010.

Kuschir, et al., describe photosensitized chemiluminescence of luminol in 6-aminophthalazine-1,4-(2H3H)-dione in *Chemical Communications* (1969) 193.

The detection of nucleic acid hybridization by non-radiative fluorescence residence energy transfer is described by Cardullo, et al., in *Proc. Natl. Acad. Sci. U.S.A.* (1988) 85:8790–8794.

Morisson, et al. describe a solution-phased detection of polynucleotides using interactive fluorescent labels and competitive hybridization in *Analytical Biochemistry* (1989) 183:231–244.

Zomer, et al. describe chemiluminogenic labels in *Analytica Chemica Acta* (1989) 227:11–19.

Morrison II discusses time-resolved detection of energy transfer: theory and application to immunoassays in *Analytical Biochemistry* (1988) 174:101–120.

U.S. Pat. No. 4,299,916 (Litman, et al. I) describes preferential signal production on a surface in immunoassays.

U.S. Pat. No. 4,233,402 (Maggio, et al.) describes reagents and methods employing channeling.

U.S. Pat. No. 4,261,968 (Ullman, et al. I) describes fluorescence quenching with immunological pairs in immunoassays.

U.S. Pat. No. 4,318,707 (Litman, et al. II) discusses a macromolecular fluorescent quencher particle in specific receptor assays.

U.S. Pat. No. 4,650,770 (Liu, et al.) discusses energy absorbing particle quenching in light-emitting competitive protein binding assays.

U.S. Pat. No. 4,654,300 (Zuk, et al.) describes a fluorescent microbead quenching assay.

U.S. Pat. No. 4,174,384 (Ullman, et al. II) describes fluorescence quenching with immunological pairs in immunoassays.

U.S. Pat. No. 4,193,983 (Ullman, et al. III) discloses labeled liposome particle compositions and immunoassays therewith.

U.S. Pat. Nos. 4,199,559 and 3,996,345 (Ullman, et al. IV and V) describes fluoroescence quenching with immunological pairs in immunoassays.

O'Connell, et al., Clin. Chem., (1985) 31(9), 1424–1426 discloses a colorimetric immunoassay for digoxin utilizing large, unilamellar phospholipid vesicles having dye entrapped in the aqueous phase of the liposome. U.S. Pat. No. 3,850,578 (McConnell); U.S. Pat. No. 4,483,921 (Yaverbaum); and U.S. Pat. No. 4,483,929 (Szoka) disclose immunoreactive liposome reagents in which antigen or antibody is bound to the surface of lipid vesicles.

U.S. Pat. Nos. 4,529,561 (Hunt, et al.); 4,522,803 (Lenk, et al.); and 4,485,054 (Mezei, et al.) disclose a variety of methods for preparing lipid vesicles.

U.S. Pat. No. 4,311,712 (Evans, et al.) discloses a process for preparing a freeze dried liposome mixture.

U.S. Pat. No. 4,588,578 (Fountain, et al.) discloses a method for the preparation of monophasic lipid vesicles and the use of such vesicles for drug delivery systems.

U.S. Pat. No. 4,576,912 discloses a method of enhancing the fluorescent level of an immunoassay using certain long-chain carriers tagged with a plurality of fluorophores.

U.S. Pat. No. 4,891,324 describes a particle with luminescer for assays.

Selective killing of T lymphocytes by phototoxic liposomes is described by Yema, et al. (1987) *Proc. Natl. Acad. Sci. USA*, 84: 246–250.

Mew, et al. in *J. of Immunology*, 130(3): 1473–1477 (1983) discloses photoimmunotherapy: treatment of animal tumors with tumor-specific monoclonal antibody-hematoporphyrin conjugates.

Optical microscopic observation of single small molecules is discussed by Hirschfeld *Applied Optics*, 15(12): 3135–3139.

SUMMARY OF THE INVENTION

The present invention is directed to methods for determining an analyte. One aspect of the invention is a method for determining an analyte where the method comprises treating a medium suspected of containing an analyte to form an intrinsically metastable species. The species is capable of diffusing in the medium and of reacting selectively with a substance in the medium capable of reacting with the metastable species brought into close proximity to the species by virtue of the presence of the analyte The method further comprises determining whether the species has reacted with the substance, the reaction thereof indicating the amount of analyte in the medium.

Another embodiment of the invention is an improvement in an assay for an analyte in a liquid medium. The assay comprises the steps of treating a medium suspected of containing the analyte to form a specific binding pair (spb) complex in relation to the presence of the the analyte and determining whether the complex is formed. The improvement comprises combining with the medium (1) a photosensitizer associated with a member of a specific binding pair and (2) a chemiluminescent compound associated with an sbp member wherein the amount of light emitted from the chemiluminescent compound upon activation of the photosensitizer is related to the amount of analyte in the medium.

Another embodiment of a method in accordance with the present invention comprises treating a medium suspected of containing an analyte under conditions such that the analyte, if present, causes a photosensitizer, and a chemiluminescent compound to come into close proximity. As a result, singlet oxygen produced by the photosensitizer can activate the chemiluminescent compound, which subsequently produces light or luminescence. The amount of light produced is related to the amount of analyte in the medium.

In another embodiment the method of the present invention for determining an analyte comprises as a first step providing a combination comprising a medium suspected of containing an analyte, a photosensitizer associated with a specific binding pair (sbp) member and a suspendible particle comprising a chemiluminescent compound. The suspendible particle has an (sbp) member bound thereto. The combination is treated to excite the photosensitizer, which is capable in its excited state of activating oxygen to a singlet states The combination is then examined for the amount of luminescence emitted. The amount of such luminescence is related to the amount of analyte in the medium. Alternatively, the chemiluminescent compound is associated with an sbp member and the suspendible particle comprises a photosensitizer and has an sbp member bound thereto.

Another embodiment is a method for determining an analyte wherein a combination is provided. The combination comprises a medium suspected of containing an analyte, a photosensitizer associated with a first sbp member and a chemiluminescent compound associated with a second sbp member. The photosensitizer is then excited and is capable of activating oxygen to a singlet state, which singlet oxygen activates the chemiluminescent compound when brought in close proximity to the photosensitizer. The luminescence emitted from the combination is related to the amount of analyte.

Another embodiment is a method for determining an analyte. The method comprises combining in an aqueous medium a sample suspected of containing an analyte, a first suspendible particle having a chemiluminescent compound incorporated therein and an sbp member bound thereto, and a second suspendible particle having incorporated therein a photosensitizer capable of activating oxygen to its singlet state where the particle has an sbp member bound thereto. The medium is then irradiated to produce the singlet state of oxygen and the amount of luminescence emitted from the medium is measured. The amount of such luminescence is related to the amount of analyte in the medium.

Another embodiment of the present invention involves compositions comprising a suspendible particle having incorporated therein a chemiluminescent compound where the particle has an sbp member bound thereto. The composition can further comprise a suspendible particle having a photosensitizer incorporated therein.

Another embodiment of the invention concerns kits comprising in packaged combination a composition that includes (1) a suspendible particle having a chemiluminescent compound where the particle has an sbp member bound thereto, and (2) a photosensitizer. The kit can further include a composition comprising a second suspendible particle comprising a photosensitizer where the particle has an sbp member bound thereto.

In another embodiment, the kit comprises (1) a chemiluminescent compound associated with a first sbp member and (2) a photosensitizer capable in its excited state of activating oxygen to its singlet state associated with a second sbp member.

DESCRIPTION OF THE SPECIFIC EMBODIMENTS

Figure 1:
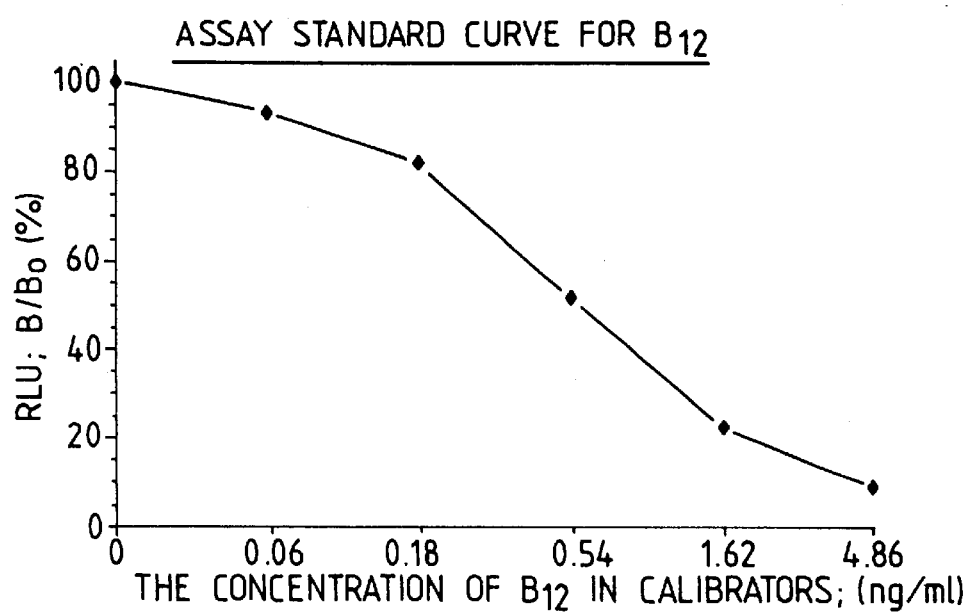
FIG. 1 is a graphic depiction of the results of an assay for vitamin $B_{12}$.

The present invention is directed to methods for determining an analyte. One aspect of the invention is a method for determining an analyte where the method comprises treating a medium suspected of containing an analyte to form an intrinsically metastable species. The species is capable of diffusing in the medium and of reacting selectively with a substance in the medium capable of reacting with the metastable species brought into close proximity to the species by virtue of the presence of the analyte. The method further comprises determining whether the species has reacted with the substance, the reaction thereof indicating the amount of analyte in the medium.

Generally, the metastable species is an excited state. The metastable species has a lifetime of less than one millisecond, usually less that 100 microseconds, more usually less than 10 microseconds. The metastable species is diffusive in the medium, i.e., it is produced at one site and migrates to another site from the site of formation where it can transfer energy or react with a molecule at that site.

The metastable species may be any reactive intermediate such as a radical ion, nitrene, carbene, from the group trans-cyclohexene, α-lactone, trimethylene methane and the like. Of particular interest are excited singlet states such as singlet oxygen, triplet states, and dioxetanes including dioxetanones and dioxetane diones. Triplet states are generally formed by combining an appropriate sensitizer such as, e,g., pyrene with an energy acceptor such as an anthracene. For example, dibromoanthracene can act as an energy acceptor which assumes a triplet state. The triplet state can proceed to transfer its energy to another molecule and initiate a detectible photochemical reaction such as the production of light, Dioxetanes such as dioxetane diones are formed from reaction of active molecules with singlet oxygen or hydrogen peroxide. For example, appropriate oxalates and hydrogen peroxide form dioxetane diones. Enzymes such as horse radish peroxidase can generate radical cations or singlet oxygen that likewise are metastable and can react with another molecule to give a detectible signal.

The presence of a specific binding pair complex can be determined by causing a metastable species to be produced by one member of the complex whereupon it can interact selectively with another member of the complex without interacting with that member when it is not within the complex.

In one aspect of the present invention a composition comprising a photosensitizer and a ligand, receptor or polynucleotide binds in an assay to a composition comprising a chemiluminescent compound and a ligand, receptor or polynucleotide. The chemiluminescent compound can react with singlet oxygen and the product formed decomposes with emission of light. The singlet oxygen is generated by the photosensitizer usually by irradiation of the photosensitizer. Singlet oxygen produced by the photosensitizer that is not bound to the composition comprising a chemiluminescent compound is unable to reach the chemiluminescent compound before undergoing decay ($t_{1/2}$ is about two microseconds in water). The composition comprising a photosensitizer that becomes bound to the composition comprising the chemiluminescent compound produces singlet oxygen that reacts with the chemiluminescent compound because such singlet oxygen can survive the short distance now realized between the photosensitizer and the chemiluminescent compound. The shortness of the distance results from the presence of an analyte in the sample. Preferably, a portion of the distance traveled by the singlet oxygen is through an organic medium where the singlet oxygen has a much longer lifetime, namely, greater than about one hundred microseconds. The analyte must modulate the binding between the composition comprising the photosensitizer and the composition comprising the chemiluminescent compound. Usually, at least one of the chemiluminescent compound and the photosensitizer is associated with a surface, particularly where the surface comprises suspendible particles.

In the assay protocol the components are provided in combination and the light produced as a function of activation of oxygen by the sensitizer will be a function of analyte concentration. Advantageously, the methods of the present invention can be carried out without heating the medium to produce light, Consequently, the assay of the present invention can be conducted at a constant temperature.

The above approach involving singlet oxygen excitation of a chemiluminescent compound in close proximity to a photosensitizer is to be distinguished from McCapra, supra. At page 4, lines 38–46, of McCapra, there is described an assay conducted in a quenching format. McCapra's assay utilizes a reactant which is capable of specifically binding with a complex of the analyte and specific binding material to which the sensitizer is conjugated, to form a sensitizer conjugate-reactant complex. A quenching moiety is attached to the reactant. When brought into close proximity to the sensitizer, the quenching moiety reduces or quenches the signal produced as a result of the excitation of bound sensitizer or reduces or quenches the transfer of electrons or energy for the excited sensitizer to an intermediate species (i.e., molecular oxygen or a leucodye). In this quenching format, the presence of analyte is related to the luminescence of the decaying dioxetans. McCapra then refers to U.S. Pat. Nos. 4,220,450 and 4,277,437, which are described above.

This quenching assay format described by McCapra involves only the quenching of the excited sensitizer and does not encompass the singlet oxygen activation of a chemiluminescent compound associated with a specific binding member.

Furthermore on page 14, lines 35–36, McCapra describes the transfer of energy from a chemiluminescent moiety to excite a sensitizer in a polynucleotide probe assay. This description by McCapra is totally distinct from the present invention, which involves the bringing together in close proximity, by virtue of an analyte being present, a photosensitizer and a chemiluminescent compound where the excited photosensitizer produces singlet oxygen, which in turn activates the chemiluminescent compound.

Before proceeding further with a description of the specific embodiments of the present invention, a number of terms will be defined and described in detail.

Analyte—the compound or composition to be detected. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The following are classes of proteins related by structure:

protamines histones albumins globulins scleroproteins phosphoproteins mucoproteins chromoproteins lipoproteins nucleoproteins glycoproteins T-cell receptors proteoglycans

HLA unclassified proteins, e.g., somatotropin, prolactin, insulin, pepsin

A number of proteins found in the human plasma are important clinically and include;

Prealbumin

Albumin $\alpha_1$-Lipoprotein $\alpha_1$-Antitrypsin $\alpha_1$-Glycoprotein

Transcortin 4.6S-Postalbumin

Tryptophan-poor
    $\alpha_1$-glycoprotein $\alpha_1$X-Glycoprotein

Thyroxin-binding globulin
Inter-α-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
β-lipoprotein
Transferrin
Hemopexin
Fibrinogen
Plasminogen
$\beta_2$-glycoprotein I
$\beta_2$-glycoprotein II
Immunoglobulin G
  (IgG) or γG-globulin
Mol. formula:
  $\gamma 2\kappa_2$ or $\gamma_2\lambda_2$
Immunoglobulin A (IgA)
  or γA-globulin
Mol. formula:
  $(\alpha_2\kappa_2)^n$ or $(\alpha_2\kappa_2)^n$
Immunoglobulin M
  (IgM) or γM-globulin
Mol. formula:
  $(\mu_2\kappa_2)^5$ or $(\mu_2\lambda_2)^5$
Immunoglobulin D (IgD)
  or γD-Globulin (γD)
Mol. formula:
  $(\delta_2\kappa_2)$ or $\delta_2\lambda_2)$
Immunoglobulin E (IgE)
  or γE-Globulin (γE)
Mol. formula:
  $(\epsilon_2\kappa_2)$ or $(\epsilon_2\lambda_2)$
Free κ and λ light chains
Complement factors;
C'1
  C'1q
  C'1r
  C'1s
  C'2
  C'3
    $\beta_1$A
    $\alpha_2$D
  C'4
  C'5
  C'6
  C'7
C'8
C'9

Important blood clotting factors include:

| International designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:
Peptide and Protein Hormones
  Parathyroid hormone
    (parathromone)
  Thyrocalcitonin
  Insulin
  Glucagon
  Relazin
  Erythropoietin
  Melanotropin
    (melancyte-stimulating) hormone; intermedin)
  Somatotropin
    (growth hormone)
  Corticotropin
    (adrenocorticotropic hormone)
  Thyrotropin
  Follicle-stimulating hormone
  Luteinizing hormone
    (interstitial cell-stimulating hormone)
  Luteomammotropic hormone
    (luteotropin, prolactin
  Gonadotropin
    (chorionic gonadotropin)
Tissue Hormones
  Secretin
  Gastrin
  Angiotensin I and II
  Bradykinin
  Human placental lactogen
Cytokines
  IL I
  IL II
  IL VI
  EGF
  TNF
  NGF
Cancer Antigens
  PSA
  CEA α-fetoprotein
Acid phosphatase
CA19.9
CA125
Tissue Specific Antigens
 alkaline phosphatase
 myoglobin
 CPK-MB
 calcitonin
 Myelin basic protein
Peptide Hormones from the Neurohypophysis
 Oxytocin
 Vasopressin
 Releasing factors (RF)
  CRF, LRF, TRF, Somatotropin-RF, GRF, FSH-RF, PIF, MIF Other polymeric materials of interest are mucopolysaccharides and polysaccharides.

Illustrative microorganisms include:

Corynebacteria

*Corynebacterium diphtheria*
Pneumococci

*Diplococcus pneumoniae*
Streptococci

*Streptococcus pyrogenes*
*Streptococcus salivarus*
Staphylococci

*Staphylococcus aureus*
*Staphylococcus albus*
Neisseria

*Neisseria meningitidis*
*Neisseria gonorrhea*
Enterobacteriaciae

*Escherichia coli*
*Aerobacter aerogenes*      The coliform
*Klebsiella pneumoniae*     bacteria
*Salmonella typhosa*
*Salmonella choleraesuis*   The Salmonellae
*Salmonella typhimurium*
*Shigella dysenteria*
*Shigella schmitzii*
*Shigella arabinotarda*
                            The Shigellae
*Shigella flexneri*
*Shigella boydii*
*Shigella sonnei*
Other enteric bacilli

*Proteus vulgaris*
*Proteus mirabilis*         Proteus species
*Proteus morgani*
*Pseudomonas aeruginosa*
*Alcaligenes faecalis*
*Vibrio cholerae*
Hemophilus-Bordetella group  *Rhizopus oryzae*

*Hemophilus influenza, H. ducryi*  *Rhizopus arrhizua* Phycomycetes
*Hemophilus hemophilus*            *Rhizopus nigricans*
*Hemophilus aegypticus*            *Sporotrichum schenkii*
*Hemophilus parainfluenza*         *Flonsecaea pedrosoi*
*Bordetella pertussis*             *Fonsecaea compact*
Pasteurellae                       *Fonsecaea dermatidis*

*Pasteurella pestis*               *Cladosporium carrionii*
*Pasteurella tulareusis*           *Phialophora verrucosa*

Brucellae                          *Aspergillus nidulans*

*Brucella melitensis*              *Madurella mycetomi*
*Brucella abortus*                 *Madurella grisea*
*Brucella suis*                    *Allescheria boydii*
Aerobic Spore-forming Bacilli      *Phialophora jeanselmei*

*Bacillus anthracis*               *Microsporum gypseum*
*Bacillus subtilis*                *Trichophyton mentagrophytes*
*Bacillus megaterium*              *Keratinomyces ajelloi*
*Bacillus cereus*                  *Microsporum canis*
Anaerobic Spore-forming Bacilli    *Trichophyton rubrum*

*Clostridium botulinum*            *Microsporum adouini*
*Clostridium tetani*               Viruses

*Clostridium perfringens*          Adenoviruses
*Clostridium novyi*                Herpes Viruses

*Clostridium septicum*             Herpes simplex
*Clostridium histolyticum*         Varicella (Chicken pox)
*Clostridium tertium*              Herpes Zoster (Shingles)
*Clostridium bifermentans*         Virus B
*Clostridium sporogenes*           Cytomegalovirus
Mycobacteria                       Pox Viruses

*Mycobacterium tuberculosis hominis*  Variola (smallpox)
*Mycobacterium bovis*                 Vaccinia
*Mycobacterium avium*                 Poxvirus bovis
*Mycobacterium leprae*                Paravaccinia
*Mycobacterium paratuberculosis*      Molluscum contagiosum
Actinomycetes (fungus-like bacteria)  Picornaviruses

*Actinomyces Isaeli*               Poliovirus
*Actinomyces bovis*                Coxsackievirus
*Actinomyces naeslundii*           Echoviruses
*Nocardia asteroides*              Rhinoviruses
*Nocardia brasiliensis*            Myxoviruses The Spirochetes                    Influenza(A, B, and C)

*Treponema pallidum Spirillum minus*  Parainfluenza (1–4)
*Treponema pertenue Streptobacillus*  Mumps Virus
*monoiliformis*                       Newcastle Disease Virus
*Treponema carateum*                  Measles Virus
*Borrelia recurrentis*                Rinderpest Virus
*Leptospira icterohemorrhagiae*       Canine Distemper Virus
*Leptospira canicola*                 Respiratory Syncytial Virus
Trypanasomes                          Rubella Virus Mycoplasmas                        Arboviruses

*Mycoplasma pneumoniae*
Other pathogens                    Eastern Equine Encephalitis Virus

*Listeria monocytogenes*           Western Equine Encephalitis Virus
*Erysipelothrix rhusiopathiae*     Sindbis Virus
*Streptobacillus moniliformis*     Chikugunya Virus
*Donvania granulomatis*            Semliki Forest Virus
*Bartonella bacilliformis*         Mayora Virus
Rickettsiae (bacteria-like parasites)  St. Louis Encephalitis Virus

*Rickettsia prowazekii*            California Encephalitis Virus
*Rlckettsia mooseri*               Colorado Tick Fever Virus
*Rickettsia rickettsii*            Yellow Fever Virus
*Rickettsia conori*                Dengue Virus
*Rickettsia australis*             Reoviruses

*Rickettsia sibiricus*             Reovlrus Types 1–3
                                   Retroviruses

*Rickettsia akari*                 Human Immunodeficiency
*Rickettsia tsutsugamushi*         Viruses I and II (HIV)
                                   Human T-cell Lymphotrophic
                                   Virus I & II (HTLV)
*Rickettsia burnetti*              Hepatitis
*Rickettsia quintana*              Hepatitis A Virus

| -continued | |
|---|---|
| Chlamydia (unclassifiable parasites bacterial/viral) | Hepatitis B Virus Hepatitis C Virus |
| Chlamydia agents (naming uncertain) | Tumor Viruses |
| Fungi | Rauscher Leukemia Virus |
| Cryptococcus neoformans | Gross Virus |
| Blastomyces dermatidis | Maloney Leukemia Virus |
| Hisoplasma capsulatum | |
| Coccidioides immitis | Human Papilloma Virus |
| Paracoccidioides brasiliensis | |
| Candida albicans | |
| Aspergillus fumigatus | |
| Mucor corymbifer | |
| (Absidia corymbifera) | |

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which include cocaine and benzyl ecgonine, their derivatives and metabolites; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids, their derivatives and metabolites.

The next group of drugs includes steroids, which includes the estrogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines; catecholamines, which includes ephedrine, L-dopa, epinephrine; narceine; papaverine; and metabolites of the above.

The next group of drugs is benzheterocyclics which include oxazepam, chlorpromazine, tegretol, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs is the hormones such as thyroxine, cortisol, triiodothyronine, testosterone, estradiol, estrone, progestrone, polypeptides such as angiotensin, LHRH, and immunosuppresants such as cyclosporin, FK506, mycophenolic acid, and so forth.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is the tricyclic antidepressants, which include imipramine, dismethylimipramine, amitriptyline, nortriptyline, protriptyline, trimipramine, chlomipramine, doxepine, and desmethyldoxepin.

The next group of drugs are the anti-neoplastics, which include methotrexate.

The next group of drugs is antibiotics, which include penicillin, chloromycetin, actinomycetin, tetracycline, terramycin, the metabolites and derivatives.

The next group of drugs is the nucleosides and nucleotides, which include ATP, AND, FMN, adenosine, guanosine, thymidine, and cytidine with their appropriate sugar and phosphate substituents.

The next group of drugs is miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Ligand analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component Clq, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme—substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgGl, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

Alkyl—a monovalent branched or unbranched radical derived from an aliphatic hydrocarbon by removal of one H atom; includes both lower alkyl and upper alkyl.

Lower alkyl—alkyl containing from 1 to 5 carbon atoms such as, e.g., methyl, ethyl, propyl, butyl, isopropyl, isobutyl, pentyl, isopentyl, etc.

Upper alkyl—alkyl containing more than 6 carbon atoms, usually 6 to 20 carbon atoms, such as, e.g., hexyl, heptyl, octyl, etc.

Alkylidene—a divalent organic radical derived from an aliphatic hydrocarbon, such as, for example, ethylidene, in which 2 hydrogen atoms are taken from the same carbon atom.

Aryl—an organic radical derived from an aromatic hydrocarbon by the removal of one atom and containing one or more aromatic rings, usually one to four aromatic rings, such as, e.g., phenyl (from benzene), naphthyl (from naphthalene), etc.

Aralkyl—an organic radical having an alkyl group to which is attached an aryl group, e.g., benzyl, phenethyl, 3-phenylpropyl, 1-naphthylethyl, etc.

Alkoxy—an alkyl radical attached to the remainder of a molecule by an oxygen atom, e.g., methoxy, ethoxy, etc.

Aryloxy—an aryl radical attached to the remainder of a molecule by an oxygen atom, e.g., phenoxy, naphthoxy, etc.

Aralkoxy—an aralkyl radical attached to the remainder of a molecule by an oxygen atom, e.g., benzoxy, 1-naphthylethoxy, etc.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbon, oxygen, nitrogen, sulfur and phosphorus, and which may or may not be bound to one or more metal atoms.

Alkylthio—an alkyl radical attached to the remainder of a molecule by a sulfur atom, e.g., methylthio, ethylthio, etc.

Arylthio—an aryl radical attached to the remainder of a molecule by a sulfur atom, e.g., phenylthio, naphthylthio, etc.

Electron-donating group—a substituent which when bound to a molecule is capable of polarizing the molecule such that the electron-donating group becomes electron poor and positively charged relative to another portion of the molecule, i.e., has reduced electron density. Such groups may be, by way of illustration and not limitation, amines, ethers, thioethers, phosphines, hydroxy, oxyanions, mercaptans and their anions, sulfides, etc.

A substituent having from 1 to 50 atoms (other than the requisite hydrogen atoms necessary to satisfy the valencies of such atoms), which atoms are independently selected from the group consisting of carbon, oxygen, nitrogen, sulfur and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are bound to carbon or one or more of each other or to hydrogen or a metal atom to form various functional groups, such as, for example, carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitrites, and the like. Illustrative of such organic radicals or groups, by way of illustration and not limitation, are alkyl, alkylidine, aryl, aralkyl, and alkyl, aryl, and aralkyl substituted with one or more of the aforementioned functionalities.

Linking group—the covalent linkage between molecules. The linking group will vary depending upon the nature of the molecules, i.e., photosensitizer, chemiluminescent compound, sbp member or molecule associated with or part of a particle, being linked. Functional groups that are normally present or are introduced on a photosensitizer or chemiluminescent compound will be employed for linking these materials to an sbp member or a particle such as a lipophilic component of a liposome or oil droplet, latex particle, silicon particle, metal sol, or dye crystallite.

For the most part, carbonyl functionalities will find use, both oxocarbonyl, e.g., aldehyde and non-oxocarbonyl (including nitrogen and sulfur analogs) e.g., carboxy, amidine, amidate, thiocarboxy and thionocarboxy.

Alternative functionalities of oxo include active halogen, diazo, mercapto, olefin, particularly activated olefin, amino, phosphoro and the like. A description of linking groups may be found in U.S. Pat. No. 3,817,837, which disclosure is incorporated herein by reference.

The linking groups may vary from a bond to a chain of from 1 to 100 atoms, usually from about 1 to 70 atoms, preferably 1 to 50 atoms more preferably 1 to 20 atoms, each independently selected from the group normally consisting of carbon, oxygen, sulfur, nitrogen and phosphorous. The number of heteroatoms in the linking groups will normally range from about 0 to 20, usually from about 1 to 15, more preferably 2 to 6. The atoms in the chain may be substituted with atoms other than hydrogen in a manner similiar to that described for the substituent having from 1 to 50 atoms. As a general rule, the length of a particular linking group can be selected arbitrarily to provide for convenience of synthesis and the incorporation of any desired group such as an energy acceptor, fluorophor, group for analysis of intersystem crossing such as a heavy atom, and the like. The linking groups may be aliphatic or aromatic, although with diazo groups, aromatic groups will usually be involved.

When heteroatoms are present, oxygen will normally be present as oxo or oxy, bonded to carbon, sulfur, nitrogen or phosphorous, nitrogen will normally be present as nitro, nitroso or amino, normally bonded to carbon, oxygen, sulfur or phosphorous; sulfur would be analogous to oxygen; while phosphorous will be bonded to carbon, sulfur, oxygen or nitrogen, usually as phosphonate and phosphate mono- or diester.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, the photosensitizer and chemiluminescent compound will have a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α,β-unsaturated ester. These functionalities will be linked to amine groups, carboxyl groups, active olefins, alkylating agents, e.g., bromoacetyl. Where an amine and carboxylic acid or its nitrogen derivative or phophoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

A group or functionality imparting hydrophilicity or water solubility—is a hydrophilic functionality, which increases wettablility of solids with water and the solubility in water of compounds to which it is bound. Such functional group or functionality can be a substituent having 1 to 50 or more atoms and can include a sulfonate, sulfate, phosphate, amidine, phosphonate, carboxylate, hydroxyl particularly polyols, amine, ether, amide, and the like. Illustrative functional groups are carboxyalkyl, sulfonoxyalkyl, $CONHOCH_2COOH$, CO-(glucosaminey, sugars, dextran, cyclodextrin, $SO_2NHCH_2COOH$, $SO_3H$, $CONHCH_2CH_2SO_3H$, $PO_3H_2$, $OPO_3H_2$, hydroxyl, carboxyl, ketone, and combinations thereof. Most of the above functionalities can also be utilized as attaching groups, which permit attachment of the photosensitizer or chemiluminescent compound to an sbp member or a support.

A group or functionality imparting lipophilicity or lipid solubility—is a lipophilic functionality, which decreases the wettability of surfaces by water and the solubility in water of compounds to which it is bound. Such functional group or functionality can contain 1 to 50 or more atoms, usually carbon atoms substituted with hydrogen or halogen and can include alkyl, alkylidene, aryl and aralkyl. The lipophilic group or functionality will normally have one to six straight or branched chain aliphatic groups of at least 6 carbon atoms, more usually at least 10 carbon atoms, and preferably at least 12 carbon atoms, usually not more than 30 carbon atoms. The aliphatic group may be bonded to rings of from 5 to 6 members, which may be alicyclic, heterocyclic, or aromacic.

Photosensitizer—a sensitizer for generation of singlet oxygen usually by excitation with light. The photosensitizer can be photoactivatable (e.g., dyes and aromatic compounds) or chemiactivated (e.g., enzymes and metal salts). When excited by light the photosensitizer is usually a compound comprised of covalently bonded atoms, usually with multiple conjugated double or triple bonds. The compound should absorb light in the wavelength range of 200–1100 nm, usually 300–1000 nm, preferably 450–950 nm, with an extinction coefficient at its absorbance maximum greater than 500 $M^{-1}$ $cm^{-1}$, preferably at least 5000 $M^{-1}$ $cm^{-1}$, more preferably at least 50,000 $M^{-1}$ $cm^{-1}$ at the excitation wavelength. The lifetime of an excited state produced following absorption of light in the absence of oxygen will usually be at least 100 nsec, preferably at least 1 μsec. In general, the lifetime must be sufficiently long to permit energy transfer to oxygen, which will normally be present at concentrations in the range of $10^{-5}$ to $10^{-3}$M depending on the medium. The sensitizer excited state will usually have a different spin quantum number (S) than its ground state and will usually be a triplet (S=1) when, as is usually the case, the ground state is a singlet (S=O). Preferably, the sensitizer will have a high intersystem crossing yield. That is, photoexcitation of a sensitizer will produce the long lived state (usually triplet) with an efficiency of at least 10%, desirably at least 40%, preferably greater than 80%. The photosensitizer will usually be at most weakly fluorescent under the assay conditions (quantum yield usually less that 0.5, preferably less that 0.1).

Photosensitizers that are to be excited by light will be relatively photostable and will not react efficiently with singlet oxygen. Several structural features are present in most useful sensitizers. Most sensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures. Typical sensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment, for example, to an sbp member. Examples of other photosensitizers that may be utilized in the present invention are those that have the above properties and are enumerated in N. J. Turro, "Molecular Photochemistry", page 132, W.A. Benjamin Inc., New York 1965.

The photosensitizers are preferably relatively non-polar to assure dissolution into a lipophilic member when the photosensitizer is incorporated in an oil droplet, liposome, latex particle, etc.

The photosensitizers useful in this invention are also intended to include other substances and compositions that can produce singlet oxygen with or, less preferably, without activation by an external light source. Thus, for example, molybdate ($MoO_4^-$) salts and chloroperoxidase and myeloperoxidase plus bromide or chloride ion (Kanofsky, *J. Biol. Chem.* (1983) 259 5596) have been shown to catalyze the conversion of hydrogen peroxide to singlet oxygen and water. Either of these compositions can, for example, be included in particles to which is bound an sbp member and used in the assay method wherein hydrogen peroxide is included as an ancillary reagebly, chloroperoxidase is bound to a surface and molybdate is incorporated in the aqueous phase of a liposome. Also included within the scope of the invention as photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1, 4-naphthalene endoperoxide, 9,10-diphenylanthracene-9, 10-endoperoxide and 5,6,11,12-tetraphenyl naphthalene 5,12-endoperoxide. Heating or direct absorption of light by these compounds releases singlet oxygen.

Support or surface—a surface comprised of a porous or non-porous water insoluble material. The surface can have any one of a number of shapes, such as strip, rod, particle, including bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

The surface will usually be polyfunctional or be capable of being polyfunctionalized or be capable of binding an oligonucleotide, an sbp member, a photosensitizer, and/or a chemiluminescent compound through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to surfaces is well known and is amply illustrated in the literature. See for example Cautrecasas, *J. Biol. Chem.* 245,3059 (1970). The length of a linking group to the oligonucleotide or sbp member may vary widely, depending upon the nature of the compound being linked, the effect of the distance between the compound being linked and the surface on the specific binding properties and the like.

Particles—particles of at least about 20 nm and not more than about 20 microns, usually at least about 40 nm and less than about 10 microns, preferably from about 0.10 to 2.0 microns diameter, normally having a volume of less than 1 picoliter. The particle may be organic or inorganic, swellable or non-swellable, porous or non-porous, having any density, but preferably of a density approximating water, generally from about 0.7 to about 1.5 g/ml, preferably suspendible in water, and composed of material that can be transparent, partially transparent, or opaque. The particles may or may not have a charge, and when they are charged, they are preferably negative. The particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may be latex particles or other particles comprised of organic or inorganic polymers; lipid bilayers, e.g., liposomes, phospholipid vesicles; oil droplets; silicon particles; metal sols; cells; and dye crystallites.

The organic particles will normally be polymers, either addition or condensation polymers, which are readily dispersible in the assay medium. The organic particles will also be adsorptive or functionalizable so as to bind at their surface, either directly or indirectly, an sbp member and to bind at their surface or incorporate within their volume a photosensitizer or a chemiluminescent compound.

The particles can be derived from naturally occurring materials, naturally occurring materials which are synthetically modified and synthetic materials. Natural or synthetic assemblies such as lipid bilayers, e.g., liposomes and non-phospholipid vesicles, are preferred. Among organic polymers of particular interest are polysaccharides, particularly cross-linked polysaccharides, such as agarose, which is available as SEPHAROSE® (Pharmacia Biotech), dextran, available as SEPHADEX® (Pharmacia Biotech) and SEPHACRYL® (Pharmacia Biotech), cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Particles may also be dispersed water insoluble dyes such as porphyrins, phthalocyanines, etc., which may also act as photosensitizers. Particles may also include diatoms, cells, viral particles, magnetosomes, cell nuclei and the like.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of being bound to an sbp member, photosensitizer, or chemiluminescent compound through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a sbp member, chemiluminescent compound or photosensitizer to the particle is employed, the manner of linking is well known and is amply illustrated in the literature. See for example Cautrecasas, *J. Biol. Chem.*, 245:3059 (1970). The length of a linking group may vary widely, depending upon the nature of the compound being linked, the nature of the particle, the effect of the distance between the compound being linked and the particle on the binding of sbp members and the analyte and the like.

The photosensitizer and/or chemiluminescent compound can be chosen to dissolve in or noncovalently bind to the surface of the particles. In this case these compounds will preferably be hydrophobic to reduce their ability to dissociate from the particle and thereby cause both compounds to associate with the same particle. This possibly can be further reduced by utilizing particles of only one composition that are associated with either the photosensitizer or chemiluminescent compound or by using two types of particles that differ in composition so as to favor association of the photosensitizer with one type of particle and association of the chemiluminescent compound with the other type of particle.

The number of photosensitizer or chemiluminescent molecules associated with each particle will on the average usually be at least one and may be sufficiently high that the particle consists entirely of photosensitizer or chemiluminescer molecules. The preferred number of molecules will be selected empirically to provide the highest signal to background in the assay. In some cases this will be best achieved by associating a multiplicity of different photosensitizer molecules to particles. Usually, the photosensitizer or chemiluminescent compound to sbp member ratio in the particles should be at least 1, preferably at least 100 to 1, and most preferably over 1,000 to 1.

Oil droplets—are fluid particles comprised of a lipophilic compound coated and stabilized with an emulsifier that is an amphiphilic molecule such as, for example, phospholipids, sphingomyelin, albumin and the like.

The phospholipids are based upon aliphatic carboxylic acid esters of aliphatic polyols, where at least one hydroxylic group is substituted with a carboxylic acid ester of from about 8 to 36, more usually of from about 10 to 20 carbon atoms, which may have from 0 to 3, more usually from 0 to 1 site of ethylenic unsaturation and at least 1, normally only 1, hydroxyl group substituted with phosphate to form a phosphate ester. The phosphate group may be further substituted with small aliphatic compounds which are of di or higher functionality, generally having hydroxyl or amino groups.

The oil droplets can be made in accordance with conventional procedures by combining the appropriate lipophilic compounds with a surfactant, anionic, cationic or nonionic, where the surfactant is present in from about 0.1 to 5, more usually from about 0.1 to 2 weight percent of the mixture and subjecting the mixture in an aqueous medium to agitation, such as sonication or vortexing. Illustrative lipophilic compounds include hydrocarbon oils, halocarbons including fluorocarbons, alkyl phthalates, trialkyl phosphates, triglycerides, etc.

An sbp member will usually be adsorbed to the surface of the oil droplet or bonded directly or indirectly to a surface component of the oil droplet. The sbp member may be incorporated into the liquid particles either during or after the preparation of the liquid particles. The sbp member will normally be present in from about 0.5 to 100, more usually 1 to 90, frequently from about 5 to 80 and preferably from about 50 to 100 mole percent of the molecules present on the surface of the particle.

The following is a list, by way of illustration and not limitation, of amphiphilic compounds, which may be utilized for stabilizing oil droplets: phosphatidyl ethanolamine, phosphatidyl choline, phosphatidyl serine, dimyristoylphosphatidyl choline, egg phosphatidyl choline, diapalmitoylphosphatidyl choline, phosphatidic acid, cardiolipin, lecithin, galactocerebroside, sphingomyelin, dicetylphosphate, phosphatldyl inositol, 2-trihexadecylammoniumethylamine, 1,3-bis(octadecyl phosphate)-propanol, stearoyloxyethylene phosphate, phospholipids, dialkylphosphates, sodium dodecyl sulfate, cationic detergents, anionic detergents, proteins such as albumin, non-ionic detergents, etc.

Other compounds may also be used which have lipophilic groups and which have been described previously. For the most part, these compounds will be alkylbenzenes, having alkyl groups of from 6 to 20 carbon atoms, usually mixtures of alkyl groups, which may be straight or branched chain, and having a carboxyl group, an hydroxylic group, a polyoxy alkylene group (alkylene of from 2 to 3 carbon atoms), carboxylic group, sulfonic acid group, or amino group. Aliphatic fatty acids may be used which will normally be of from about 10 to 36, more usually of from about 12 to 20 carbon atoms. Also, fatty alcohols having the carbon limits indicated for the fatty acids, fatty amines of similar carbon limitations and various steroids may also find use.

The oil droplets can comprise a fluorocarbon oil or a silicone oil (silicon particle). Such droplets are described by Giaever in U.S. Pat. Nos. 4,634,681 and 4,619,904 (the disclosures of which are incorporated herein in their entirety). These droplets are formed by dispersing a fluorocarbon oil or silicone oil in an aqueous phase. The droplets are prepared by placing a small amount of the selected oil (generally, such oils are commercially available) in a container with a larger amount of the aqueous phase. The liquid system is subjected to agitation to bring about emulsification and then centrifuged. The homogeneous phase is removed and the residual droplets are resuspended in an aqueous buffered medium. The above centrifugation and decantation steps can be repeated one or more times before the droplets are utilized.

Sbp members can be bound to the droplets in a number of ways. As described by Giaever, the particular sbp member, particularly a proteinoceous sbp member, can be coated on the droplets by introducing an excess of the sbp member into the aqueous medium prior to or after the emulsification step. Washing steps are desirable to remove excess sbp member. Functionalization of the oil introduces functionalities described above for linking to sbp members. Such functionalities can also be employed to link the droplets to a photosensitizer or a chemiluminescent compound. On the other hand, the photosensitizer or chemiluminescent compound will frequently be chosen to be soluble in the oil phase of the oil droplet and will not be covalently bound. When the oil is a fluorocarbon, a fluorinated photosensitizer or chemiluminescent compound will often be more soluble than the corresponding unfluorinated derivation.

Other oil droplets described by Giaever also find use in the present invention.

Liposomes—microvesicles of approximately spherical shape and are one of the preferred materials for use in the present invention. The liposomes have a diameter that is at least about 20 nm and not more than about 20 microns, usually at least about 40 nm and less than about 10 microns. Preferably, the diameter of the liposomes will be less than about two microns so as to limit settling or floatation.

The outer shell of a liposome consists of an amphiphilic bilayer that encloses a volume of water or an aqueous solution. Liposomes with more than one bilayer are referred to as multilamellar vesicles. Liposomes with only one bilayer are called unilamellar vesicles. Multilamellar vesicles are preferred in the present invention when using a lipophilic photosensitizer or chemiluminescent compound because of their ability to incorporate larger quantities of these materials than unilamellar vesicles. The amphiphilic bilayer is frequently comprised of phospholipids. Phospholipids employed in preparing particles utilizable in the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Particularly preferred phospholipids include L-α-palmitoyl oleoyl-phosphatidylcholine (POPC), palmitoyl oleoylphosphatidyl-glycerol (POPG), L-α-dioleoylphosphatidylglycerol, L-α(dioleoyl)-phosphatidyl ethanolamine (DOPE) and L-α(dioleoyl)-phosphatidyl β-(4-(N-maleimidomethyl)-cyclohexane-1-carboxyamido) ethanol (DOPE-MCC).

The phospholipids in the bilayer may be supplemented with cholesterol and may be replaced with other amphiphilic compounds that have a polar head group, usually charged, and a hydrophobic portion usually comprised of two linear hydrocarbon chains. Examples of such substitutents include dialkylphosphate, dialkoxypropylphosphates wherein the alkyl groups have linear chains of 12–20 carbon atoms, N-(2,3-di( 9-(Z)-octa-decenyloxy))-prop-1-yl-N,N,N-trimethyl-ammonium chloride (DOTMA), as disclosed in U.S. patent application Ser. No. 811,146 filed on Dec. 19, 1985, which is hereby incorporated herein by reference, sphingomyelin, cardiolipin, and the like.

Liposomes utilized in the present invention preferably have a high negative charge density to stabilize the suspension and to prevent spontaneous aggregation.

For use in the present invention the liposomes should be capable of binding to an sbp member and be capable of having a photosensitizer or chemiluminescent compound associated with either the aqueous or the nonaqueous phase. The liposomes utilized in the present invention will usually have sbp members bound to the outer surface of the lipid vesicle.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is usable as a final step during the production of the liposomes. U.S. Pat. No. 4,529,561 discloses a method of extruding liposomes under pressure through a uniform pore-size membrane to improve size uniformity.

Preparation of liposomes containing a hydrophobic or amphiphilic photosensitizer or a chemiluminescent compound dissolved in the lipid bilayer can be carried out in a variety of methods, including a method described by Olsen, et al., *Biochemica et Biophysica Acta*, 557(9), 1979. Briefly, a mixture of lipids containing the appropriate compound in an organic solvent such as chloroform is dried to a thin film on the walls of a glass vessel. The lipid film is hydrated in an appropriate buffer by shaking or vortexing. Thereafter, the lipid suspension is extruded through a series of polycarbonate filter membranes having successively smaller pore sizes. For example, 2.0, 1.0, 0.8, 0.6, 0.4, and 0.2 microns. Repeated filtration through any of the filters, and in particular through the smallest filter, is desirable. The liposomes can be purified by, for example, gel filtration, such as through a column of SEPHACRYL® S-1000 (Pharmacia Biotech). The column can be eluted with buffer and the liposomes collected. Storage in the cold prolongs shelf-life of the liposomes produced by this method. Alternatively the photosensitizer or chemiluminescent compound can be added to the liquid suspension following preparation of the liposomes.

Labeling of droplets and liposomes will often involve, for example, inclusion of thiol or maleimide or biotin groups on the molecules comprising the lipid bilayer. Photosensitizers, chemiluminescent molecules or sbp members may then be bound to the surface by reaction of the particles with one of these materials that is bound to a sulfhydryl reactive reagent, a sulfhydryl group, or avidin, respectively. Sulfhydryl reactive groups include alkylating reagents such as bromoacetamide and maleimide.

Sbp members can be attracted to the surface of the liposome particles by weak hydrophobic interactions, however such interactions are not generally sufficient to withstand the shear force encountered during incubation and washing. It is preferable to covalently bond sbp members to a liposome particle that has been functionalized, for example by use of DOPE-MCC, as shown above, by combining said liposome with the selected sbp member functionalized with a mercaptan group. For example, if the sbp member is an antibody, it may be reacted with S-acetyl-mercaptosuccinic anhydride (SAMSA) and hydrolyzed to provide a sulfhydryl modified antibody.

Latex particles—"Latex" signifies a particulate water suspendible water insoluble polymeric material usually having particle dimensions of 20 nm to 20 μm, more preferably 100 to 1000 nm in diameter. The latex is frequently a substituted polyethylene such as: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyrridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The association of the photosensitizer or chemiluminescent compound with latex particles utilized in the present invention may involve incorporation during formation of the particles by polymerization but will usually involve incorporation into preformed particles, usually by noncovalent dissolution into the particles. Usually a solution of the chemiluminescent compound or sensitizer will be employed. Solvents that may be utilized include alcohols, including ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the compounds into the particles and are particularly suitable. The solvents may be used singly or in combination. Particularly preferred solvents for incorporating photosensitizer are those that will not quench the triplet excited state of the photosensitizer either because of their intrinsic properties or because they can subsequently be removed from the particles by virtue of their ability to be dissolved in a solvent such as water that is insoluble in the particles. Aromatic solvents are preferred, and generally solvents that are soluble in the particle. For incorporating chemiluminescent compounds in particles a solvent should be selected that does not interfere with the luminescence because of their intrinsic properties or ability to be removed from the particles. Frequently, aromatic solvents will also be preferred. Typical aromatic solvents include dibutylphthalate, benzonitrile, naphthonitrile, dioctylterephthalate, dichlorobenzene, diphenylether, dimethoxybenzene, etc.

Except when the photosensitizer or chemiluminescent compound is to be covalently bound to the particles, it will usually be preferable to use electronically neutral photosensitizers or chemiluminescent compounds. It is preferable that the liquid medium selected does not soften the polymer beads to the point of stickiness. A preferred technique comprises suspending the selected latex particles in a liquid medium in which the photosensitizer or chemiluminescent compound has at least limited solubility. Preferably, the concentrations of the photosensitizer and chemiluminescent compound in the liquid media will be selected to provide particles that have the highest efficiency of singlet oxygen formation and highest quantum yield of emission from the chemiluminescent compound in the media but less concentrated solutions will sometimes be prefered. Distortion or dissolution of the particles in the solvent can be prevented by adding a miscible cosolvent in which the particles are insoluble.

Generally, the temperature employed during the procedure will be chosen to maximize the singlet oxygen formation ability of the photosensitizer labeled particles and the quantum yield of the chemiluminescent compound particles with the proviso that the particles should not melt or become aggregated at the selected temperature. Elevated temperatures are normally employed. The temperatures for the procedure will generally range from 20° C. to 200° C., more usually from 50° C. to 170° C. It has been observed that some compounds that are nearly insoluble at room temperature, are soluble in, for example, low molecular weight alcohols, such as ethanol and ethylene glycol and the like, at elevated temperatures. Carboxylated modified latex particles have been shown to tolerate low molecular weight alcohols at such temperatures.

An sbp member may be physically adsorbed on the surface of the latex particle or may be covalently bonded to the particle. In cases wherein the sbp member is only weakly bound to the surface of the latex particle, the binding may in certain cases be unable to endure particle-to-particle shear forces encountered during incubation and washings. Therefore, it may be preferable to covalently bond sbp members to the latex particles under conditions that will minimize adsorption. This may be accomplished by chemically activating the surface of the latex. For example, the N-hydroxysuccinimide ester of surface carboxyl groups can be formed and the activated particles to reduce nonspecific binding of assay components to the particle surface, are then contacted with a linker having amino groups that will react with the ester groups or directly with an sbp member that has an amino group. The linker will usually be selected to reduce nonspecific binding of assay components to the particle surface and will preferably provide suitable functionality for both attachment to the latex particle and attachment of the sbp member. Suitable materials include maleimidated aminodextran (MAD), polylysine, aminosaccharides, and the like. MAD can be prepared as described by Hubert, et al., *Proc. Natl. Acad. Sci.*, 75(7), 3143, 1978.

In one method, MAD is first attached to carboxyl-containing latex particles using a water soluble carbodiimide, for example, 1-(3-dimethylaminopropyl)-3-ethyl carbodiimide. The coated particles are then equilibrated in reagents to prevent nonspecific binding. Such reagents include proteins such as bovine gamma globulin (BGG), and detergent, such as TWEEN® 20 (ICI Americas, Inc.), TRITON X-100® (Adam and Han's Company) and the like. A sbp member having a sulfhydryl group, or suitably modified to introduce a sulfhydryl group, is then added to a suspension of the particles, whereupon a covalent bond is formed between the sbp member and the MAD on the particles. Any excess unreacted sbp member can then be removed by washing.

Metal sols—are those particles comprised of a heavy metal, i.e., a metal of atomic number greater than 20 such as a Group IB metal, e.g., gold or silver or chalcogens such as selenium or tellurium.

Metal sol particles are described, for example, by Leuvering in U.S. Pat. No. 4,313,734, the disclosure of which is incorporated herein by reference in its entirety. Such sols include colloidal aqueous dispersion of a metal, metal compound, or polymer nuclei coated with a metal or metal compound.

The metal sols may be of metals or metal compounds, such as metal oxides, metal hydroxides and metal salts or of polymer nuclei coated with metals or metal compounds. Examples of such metals are platinum, gold, silver mercury, lead, palladium, and copper, and of such metal compounds are silver iodide, silver bromide, copper hydrous oxide, iron oxide, iron hydroxide or hydrous oxide, aluminum hydroxide or hydrous oxide, chromium hydroxide or hydrous oxide, vanadium oxide, arsenic sulphide, manganese hydroxide, lead sulphide, mercury sulphide, barium sulphate and titanium dioxide. In general, the metals or metal compounds useful may be readily demonstrated by means of known techniques.

It is sometimes advantageous to use sols comprised of dispersed particles consisting of polymer nuclei coated with the above mentioned metals or metal compounds. These particles have similar properties as the dispersed phase of pure metals or metal compounds, but size, density and metal contact can be optimally combined.

The metal sol particles may be prepared in a large number of ways which are in themselves known. For example, for the preparation of a gold sol Leuvering refers to an article by G. Frens in *Nature Physical Science* 241, 20 (1973).

The metal sol particles can be modified to contain various functional groups as described above for linking to an sbp member or a photosensitizer or a chemiluminescent compound. For example, polymeric bonding agents can be used to coat the particles such as polymers containing thiol groups that bond strongly to many heavy metals or silylating agents that can bond and form polymeric coatings as, for example, by reaction of metal particles with trialkoxy aminoalkylsilanes as described in EPO Patent Appl. 84400952.2 by Advanced Magnetics for coating magnetic particles.

Dye crystallites—microcrystals of pure or mixed solid water insoluble dyes, preferably dyes that can serve as the photosensitizers described above. The dye crystallites useful in the present invention have a size range of 20 nm to 20 μm.

One method for preparing dye crystallites is described in U.S. Pat. No. 4,373,932 (Gribnau, et al.), the disclosure of which is incorporated herein by reference in its entirety. Gribnau describes colloidal dye particles and aqueous dispersions of a hydrophobic dye or pigment, which may have an immunochemically reactive component directly or indirectly attached. The dye particles are prepared in general by dispersing a dye in water and then centrifuging. A dye pellet is obtained and resuspended in water, to which glass beads are added. This suspension is rolled for several days at room temperature. The liquid is decanted and centrifuged, and the dye particles are obtained after aspiration of the liquid.

Another method for preparing dye crystallites is by slow addition of a solution of the dye in a water miscible solvent to water. Another method is by sonication of a suspension of the solid dye in water.

Binding of sbp members to the dye particles can be achieved by direct or indirect adsorption or covalent chemical attachment. The latter is governed by the presence of suitable functional groups in any coating material and in the dye. For example, functional groups can be introduced onto the surface of a dye crystallite by coupling a compound containing a diazotized aromatic amino group and the desired functional group to a phenolic or anilino group of the dye.

Where the dye has a carboxyl group, the dye crystallite can be activated by a carbodiimide and coupled to a primary amino component. Aliphatic primary amino groups and hydroxyl groups can be activated, for example, by cyanogen bromide or halogen-substituted di- or tri-azines, after which attachment with a primary amino component or with, for example, a component containing a —SH, or —OH or group can take place. Use can also be made of bifunctional reactive compounds. For example, glutaraldehyde can be used for the mutual coupling of primary amino components of the dye and an sbp member, and, for example, a hetero-bifunctional reagent such as N-succinimidyl 3-(2-pyridyldithio) propionate can be employed for the coupling of a primary amino component to a component containing a thiol group.

Chemiluminescent compound—a substance that undergoes a chemical reaction with singlet oxygen to form a metastable intermediate that can decompose with the simultaneous or subsequent emission of light within the wavelength range of 250 to 1200 nm. Emission will usually occur without the presence of an energy acceptor or catalyst to cause decomposition and light emission. Preferably, the intermediate decomposes spontaneously without heating or addition of ancillary reagents following its formation. However, addition of a reagent after formation of the intermediate or the use of elevated temperature to accelerate decomposition will be required for some chemiluminescent compounds. The chemiluminescent compounds are usually electron rich compounds that react with singlet oxygen, frequently with formation of dioxetanes or dioxetanones. Exemplary of such compounds are enol ethers, enamines, 9-alkylidenexanthans, 9-alkylidene-N-alkylacridans, aryl vinyl ethers, dioxenes, arylimidazoles and lucigenin. Other chemiluminescent compounds give intermediates upon reaction with singlet oxygen, which subsequently react with another reagent with light emission. Exemplary compounds are hydrazides such as luminol and oxalate esters.

The chemiluminescent compounds of interest will generally emit at wavelengths above 300 nanometers and usually above 400 nm. Compounds that alone or together with a fluorescent molecule emit light at wavelengths beyond the region where serum components absorb light will be of particular use in the present invention. The fluorescence of serum drops off rapidly above 500 nm and becomes relatively unimportant above 550 nm. Therefore, when the analyte is in serum, chemiluminescent compounds that emit light above 550 nm, preferably above 600 nm are of particular interest. In order to avoid autosensitization of the chemiluminescent compound, it is preferable that the chemiluminescent compounds do not absorb light used to excite the photosensitizer. Since it will generally be preferable to excite the sensitizer with light wavelengths longer than 500 nm, it will therefore be desirable that light absorption by the chemiluminescent compound be very low above 500 nm.

Where long wave length emission from the chemiluminescent compound is desired, a long wavelength emitter such as a pyrene, bound to the chemiluminescent compound can be used. Alternatively, a fluorescent molecule can be included in the medium containing the chemiluminescent compound. Preferred fluorescent molecules will be excited by the activated chemiluminescent compound and emit at a wavelength longer than the emission wavelength of the chemiluminescent compound, usually greater that 550 nm. It is usually also desirable that the fluorescent molecules do not absorb at the wavelengths of light used to activate the photosensitizer. Examples of useful dyes include rhodamine, ethidium, dansyl, Eu(fod)$_3$, Eu(TTA)$_3$, Ru(bpy)$_3^{++}$ (wherein bpy=2,2'-dipyridyl, etc. In general these dyes act as acceptors in energy transfer processes and preferably have high fluorescent quantum yields and do not react rapidly with singlet oxygen. They can be incorporated into particles simultaneously with the incorporation of the chemiluminescent compound into the particles. The electron rich olefins generally have an electron donating group in conjugation with the olefin:

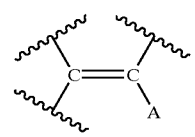

(1)

wherein A is an electron donating group such as, for example, N(D)$_2$, OD, p-[C$_6$H$_4$N(D)$_2$]$_2$, furanyl, n-alkylpyrrolyl, 2-indolyl, etc., where D can, for example, be alkyl or aryl, and either bound directly to the olefinic carbon or bound by the intermediacy of other conjugated double bonds, substitutents of 1 to 50 atoms, which may be taken together to form one or more rings, which are fused or unfused, e.g., cycloalkyl, phenyl, naphthyl, anthracyl, acridanyl, adamantyl, and so forth.

Enol ethers of use in this invention generally have the structure:

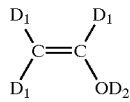
(2)

wherein the $D_1$'s are taken independently and are selected from the group consisting of H and substituents of 1 to 50 atoms, preferably, aryl, hydroxyaryl, aminoaryl, t-alkyl, H, alkoxy, heteroaryl, etc., and may be taken together with one or both of the carbon atoms to form a ring such as a cycloalkene, adamantylidene, 7-norbornylidene and the like, and $D_2$ is preferably alkyl or aryl. Exemplary enol ethers, by way of illustration and not limitation, are 2,3-diaryl-4,5-dihydrodioxenes:

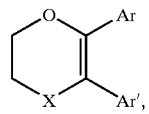
(3)

where X=O,S, or $ND_2$ and Ar and Ar' are aryl including substituted aryl wherein at least one substituent is present as amino, ether or hydroxyl group.

9-(Dialkoxymethylidene)-xanthene:

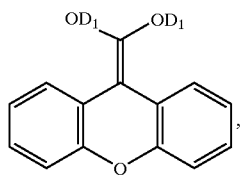
(4)

Alkoxyvinylpyrene:

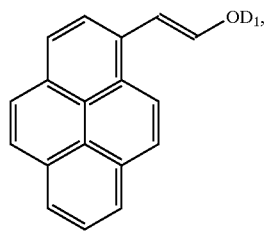
(4A)

9-Alkoxymethylidine-10-alkylacridan:

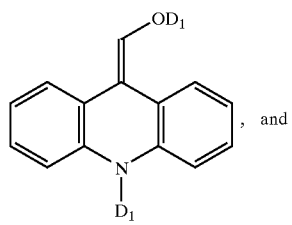
(5)

and

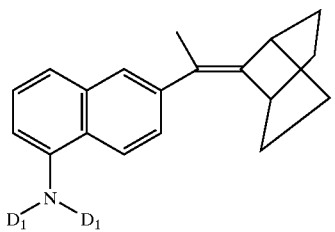
(5A)

Vinyl sulfides of use in this invention generally include the above mentioned enol ethers wherein the oxygen atom is replaced by a sulfur atom.

Enamines of use in this invention generally have the structure:

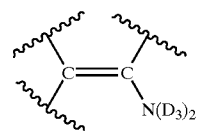
(6)

wherein $D_3$ may be independently alkyl or aryl and the remaining substituents on the olefin are selected from the group consisting of H and substituents of 1 to 50 atoms, preferably aryl, hydroxyaryl, aminoaryl, t-alkyl, H, alkoxy, heteroaryl, etc.

Exemplary enamines by way of illustration and not limitation are dialkylaminovinylpyrene:

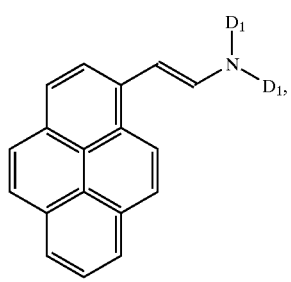
(6A)

dialkylaminovinyl-9,10-diphenylanthracene

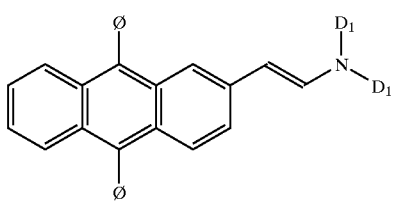
(6B)

wherein φ=phenyl and so forth.-

9-Alkylidene-N-alkylacridans generally have the structure:

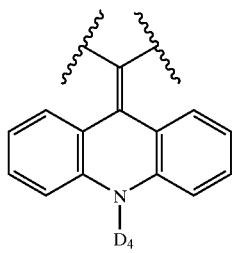

(7)

wherein $D_4$ is alkyl and the remaining substituents on the olefin are selected from the group consisting of H and substituents of 1 to 50 atoms, preferably, phenyl, aryl, alkoxyaryl, aminoaryl, t-alkyl, H, alkoxy, heteroaryl, etc., and may be taken together to form a ring such as, for example, adamantyl, cyclopentyl, 7-norbornyl, and the like.

Exemplary acridans by way of illustration and not limitation are substituted 9-benzylidene-10-methyl acridan, and 9-diphenylmethylene-10-methyl acridan described by Singer, et al., *J. Am. Chem. Soc.* 102: 3823(1983), and McCapra, *Chem. Comm.* 944(1977), 9-methylidene-10-methylacridans described by E. White, *Chem. Letters* 1491 (1979).

Dioxetanes formed by the reaction of singlet oxygen with the chemiluneral structure where the substituents on the carbon (C) atoms are those present on the corresponding olefin:

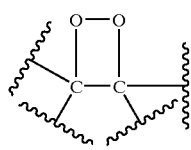

(8)

some of which decompose spontaneously, others by heating and/or by catalysis usually by an electron rich energy acceptor, with the emission of light. For some cases the dioxetane is spontaneously converted to a hydroperoxide whereupon basic pH is required to reform the dioxetane and permit decomposition and light emission.

Another family of chemiluminescent compounds is 2,3-dihydro-1,4-phthalazinediones. The most popular compound is luminol, which is the 5-amino compound. Other members of the family include substituted 6-amino, 5-amino-6,7,8-trimethoxy and the dimethylamino[ca]benz analog. These compounds are oxidized by singlet oxygen in a multistep reaction that results in decomposition with formation of a phthalate derivative and light emission.

Another family of chemiluminescent compounds is the 2,4,5-triphenylimidazoles, with lophine as the common name for the parent compound. Chemiluminescent analogs include para-dimethylamino and -methoxy substituents.

The next group of chemiluminescent compounds includes bis arylene compounds including the bis-9,9'-acridylidene and the 10,10'-dimethyl derivative thereof described by Singer, *J. Org. Chem.* 41:2685(1976), lucigenin, and bis-9, 9'-xanthylidine.

Other chemiluminescent compounds that satisfy the requirements given above may be found in European Patent Application 0,345,776.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like. When the photosensitizer is activated chemically rather than by irradiation, hydrogen peroxide will often be included as an ancillary reagent. When it is desired to shift the emission wavelength of the chemiluminescent compound to longer wavelength or catalyse the decomposition of its oxygen-activated form, a fluorescent molecule may be employed.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

One aspect of the present invention is a method for determining an analyte. The method comprises treating a medium suspected of containing an analyte under conditions such that the analyte, if present, affects the amount of a photosensitizer and a chemiluminescent compound that can come into close proximity wherein the short-lived singlet oxygen generated by the photosensitizer can react with the chemiluminescent compound prior to its spontaneous decay. The method further comprises measuring the intensity of luminescence produced by the chemiluminescent compound. The intensity of luminescence produced is related to the amount of analyte in the medium. The chemiluminescent compound is capable of activation by singlet oxygen, and the photosensitizer catalyzes the formation of singlet oxygen usually in response to photoexcitation followed by energy transfer to molecular oxygen. Often a surface will be brought into close proximity with the photosensitizer and chemiluminescent compound, wherein the surface will preferably be the surface of suspendible particles. The product formed by the activation of the chemiluminescent compound decomposes, preferably spontaneously, with emission of light.

The invention is predicated on an analyte causing or inhibiting molecules of the photosensitizer and the chemiluminescent compound to be closer to each other than their average distance in the bulk solution of the assay medium. This partitioning will depend upon the amount of analyte present in the sample to be analyzed. The photosensitizer molecules that do not become associated with the chemiluminescent compound produce singlet oxygen that is unable to reach the chemiluminescent compound before undergoing decay in the aqueous medium. However, when the photosensitizer and the chemiluminescent compound come in close proximity with each other in response to the amount of the analyte, the singlet oxygen produced upon irradiation of the photosensitizer can activate the chemiluminescent compound before undergoing decay. Because numerous chemiluminescent compound molecules and/or photosensitizer molecules can be associated with a surface and because diffusion is restricted at a surface, the presence of a surface in conjunction with the photosensitizer and chemiluminescent compound can increase the efficiency of, or action of, singlet oxygen with the chemiluminescent compound prior to decay. The use of a surface that is brought in proximity of the chemiluminescent compound and photosensitizer as a function of the presence of analytes is, therefore, preferred.

The subject assay provides for a convenient method for detecting and measuring a wide variety of analytes in a simple, efficient, reproducible manner, which can employ simple equipment for measuring the amount of light produced during the reaction.

The amount of photosensitizer that comes in close proximity to the chemiluminescent compound is affected by the presence of analyte by virtue of the photosensitizer and chemiluminescent compound each being associated with an sbp member. This may be accomplished in a number of ways and the term "associated with" is defined thereby. The photosensitizer and chemiluminescent compound may contain functionalities for covalent attachment to sbp members or the sbp members, or groups capable of binding to sbp members, may contain functionalities for attaching to the photosensitizer and/or chemiluminescent compound. The attachment may be accomplished by a direct bond between the two molecules or a linking group can be employed between an sbp member and the photosensitizer or chemiluminescent compound. In another embodiment either or both of the photosensitizer and chemiluminescent compound can be bound to surfaces or incorporated in particles, to which are also attached sbp members. In both cases each of the sbp members is capable of binding directly or indirectly to the analyte or an assay component whose concentration is affected by the presence of the analyte. The photosensitizer and chemiluminescent compound can be incorporated into particles by virtue of being soluble in at least one phase of the particles, in which case the photosensitizer and chemiluminescent compound will be at much higher concentration within the particle than in the bulk assay medium. When the photosensitizer and chemiluminescent compound are covalently bound to particles, the photosensitizer and chemiluminescent compound or the particles, or components thereof, are functionalized to provide a means of attaching the photosensitizer and chemiluminescent compounds and the particles. For particles that are oil droplets or liposomes the photosensitizer and chemiluminescent compound can be attached to one or more long hydrocarbon chains, each generally having at least 10 to 30 carbon atoms. If the particles are droplets of a fluorocarbon, the photosensitizer or chemiluminescent compound incorporated into these particles may be fluorinated to enhance solubility and reduce exchange into other particles bound with the other label, and the hydrocarbon chain used for linking will preferably be replaced with a fluorocarbon chain. For silicon fluid particles the photosensitizer and chemiluminescent compound can be bound to a polysiloxane. In order to maximize the number of photosensitizer or chemiluminescent compound molecules per particle, it will usually be desirable to minimize the charge and polarity of the photosensitizer or chemiluminescent compound so that it resides within the non-aqueous portion of the particle. When the particle is a liposome and it is desired to retain the photosensitizer or chemiluminescent compound in the aqueous phase of the liposome, it will be preferred to use photosensitizers or chemiluminescent compounds that are highly polar or charged.

No matter how the photosensitizer and chemiluminescent compound are bound, it is critical that neither compound is capable of dissociating from its sbp member and becoming associated with the sbp member bound to the other member of the photosensitizer and chemiluminescent compound pair during the course of the assay. Thus, dissociation of these compounds from their respective sbp members must be slow relative to the time required for the assay.

The chemiluminescent compound may be bound to a sbp member that is capable of binding directly or indirectly to the analyte or to an assay component whose concentration is affected by the presence of the analyte. The term "capable of binding directly or indirectly" means that the designated entity can bind specifically to the entity (directly) or can bind specifically to a specific binding pair member or to a complex of two or more sbp members which is capable of binding the other entity (indirectly).

The surface generally has an sbp member bound to it. Preferably, the chemiluminescent compound is associated with the surface, usually within a suspendible particle. This sbp member is generally capable of binding directly or indirectly to the analyte or a receptor for the analyte. When the sbp members associated with the photosensitizer and the chemiluminescent compound are both capable of binding to the analyte, a sandwich assay protocol results. When one of the sbp members associated with the photosensitizer or chemiluminescent compound can bind both the analyte and an analyte analog, a competitive assay protocol can result. The attachment to a surface or incorporation in a particle of the chemiluminescent compound is governed generally by the same principles described above for the attachment to, or the incorporation into, a particle of the photosensitizer.

The photosensitizer is usually caused to activate the chemiluminescent compound by irradiating the medium containing the above reactants. The medium must be irradiated with light having a wavelength with energy sufficient to convert the photosensitizer to an excited state and thereby render it capable of activating molecular oxygen to singlet oxygen. The excited state for the photosensitizer capable of exciting molecular oxygen is generally a triplet state which is more than about 20, usually at least 23, Kcal/mol more energetic than the photosensitizer ground state. Preferably, the medium is irradiated with light having a wavelength of about 450 to 950 nm although shorter wavelengths can be used, for example, 230–950 nm. The luminescence produced may be measured in any convenient manner such as photographically, visually or photometrically to determine the amount thereof, which is related to the amount of analyte in the medium.

Although it will usually be preferable to excite the photosensitizer by irradiation with light of a wavelength that is efficiently absorbed by the photosensitizer, other means of excitation may be used as for example by energy transfer from an excited state of an energy donor such as a second photosensitizer. When a second photosensitizer is used, wavelengths of light can be used which are inefficiently absorbed by the photosensitizer but efficiently absorbed by the second photosensitizer. The second photosensitizer may be bound to an assay component that is associated, or becomes associated, with the first photosensitizer, for example, bound to a surface or incorporated in the particle having the first photosensitizer. When a second photosensitizer is employed it will usually have a lowest energy triplet state at higher energy than the lowest energy triplet state of the first photosensitizer.

The 632.6 nm emission line of a helium-neon laser is an inexpensive light source for excitation. Photosensitizers with absorption maxima in the region of about 620 to about 650 nm are compatible with the emission line of a helium-neon laser and are, therefore, particularly useful in the present invention.

Another aspect of the invention is a method for determining an analyte, which comprises: (a) providing in combination (1) a medium suspected of containing analyte, (2) a photosensitizer capable in its excited state of activating oxygen to a singlet state, the photosensitizer being associated with a sbp member, and (3) a suspendible particle comprising a chemiluminescent compound wherein the particle has an sbp member bound thereto, (b) treating the combination with light to excite the photosensitizer and (c) examining the combination for the amount of luminescence emitted therefrom. The amount of luminescence emitted is related to the amount of analyte in the medium. Preferably, the chemiluminescent compound is incorporated in a suspendible particle and the sbp member is bound to the particle. More preferably, the photosensitizer is incorporated in a second suspendible particle which has an sbp member bound to it.

The method and compositions of the invention may be adapted to most assays involving sbp members such as ligand-receptor; e.g., antigen-antibody reactions; polynucleotide binding assays, and so forth. The assays may be homogeneous or heterogeneous, competitive or noncompetitive. The assay components, chemiluminescent compound and photosensitizer, can be utilized in a number of ways with (1) a surface, when employed, (2) nucleic acid or receptor and (3) nucleic acid or ligand. The association may involve covalent or non-covalent bonds. Those skilled in the art will be able to choose appropriate associations depending on the particular assay desired in view of the foregoing and the following illustrative discussion.

In a homogeneous assay approach, the sample may be pretreated if necessary to remove unwanted materials. The reaction for a noncompetitive sandwich type assay can involve an sbp member, (e.g., an antibody, nucleic acid probe, receptor or ligand) complementary to the analyte and associated with a chemiluminescent compound; a photosensitizer associated with an sbp member, (e.g., antibody, nucleic acid probe, receptor or ligand) that is also complementary to the analyte; the sample of interest; and any ancillary reagents required. Preferably, one or both of the photosensitizer and the chemiluminescent compound are incorporated in particles to which the sbp members are attached. In a competitive protocol one sbp member can be a derivative of the analyte and the other sbp member can be complementary to the analyte, e.g., an antibody. In either protocol the components may be combined either simultaneously or wholly or partially sequentially. The ability of singlet oxygen produced by an activated photosensitizer to react with the chemiluminescent compound is governed by the binding of an sbp member to the analyte. Hence, the presence or amount of analyte can be determined by measuring the amount of light emitted upon activation of the photosensitizer by irradiation, heating or addition of a chemical reagent, preferably by irradiation. Both the binding reaction and detection of the extent thereof can be carried out in a homogeneous solution without separation. This is an advantage of the present invention over prior art methods utilizing chemiluminescence.

In a heterogeneous assay approach, the assay components comprise a sample suspected of containing an analyte which is an sbp member; an sbp member bound to a support, which may be either a non-dispersible surface or a particle having associated with it one member of a group consisting of the chemiluminescent compound and the photosensitizer; and an sbp member having the other member of the group associated with it wherein the sbp members can independently, either directly or indirectly, bind the analyte or a receptor for the analyte. These components are generally combined either simultaneously or wholly or partially sequentially. The surface or particles are then separated from the liquid phase and either the separated phase or the liquid phase is subjected to conditions for activating the photosensitizer, usually by irradiating the particular phase in question, and measuring the amount of light emitted.

The binding reactions in an assay for the analyte will normally be carried out in an aqueous medium at a moderate pH, generally that which provides optimum assay sensitivity. Preferably, the activation of the photosensitizer will also be carried out in an aqueous medium. However, when a separation step is employed, non-aqueous media such as, e.g., acetonitrile, acetone, toluene, benzonitrile, etc. and aqueous media with pH values that are very high, i.e., greater than 10.0, or very low, i.e., less than 4.0, usually very high, can be used. As explained above, the assay can be performed either without separation (homogeneous) or with separation (heterogeneous) of any of the assay components or products.

The aqueous medium may be solely water or may include from 0.01 to 80 volume percent of a cosolvent but will usually include less than 40% of a cosolvent when an sbp member is used that is a protein. The pH for the medium of the binding reaction will usually be in the range of about 4 to 11, more usually in the range of about 5 to 10, and preferably in the range of about 6.5 to 9.5. When the pH is not changed during the generation of singlet oxygen the pH will usually be a compromise between optimum binding of the binding members and the pH optimum for the production of signal and the stability of other reagents of the assay. When elevated pH's are required for signal production, a step involving the addition of an alkaline reagent can be inserted between the binding reaction and generation of singlet oxygen and/or signal production. Usually the elevated pH will be greater than 10, usually 10–14. For heterogenous assays non-aqueous solvents may also be used as mentioned above, the main consideration being that the solvent not react efficiently with singlet oxygen.

Various buffers may be used to achieve the desired pH and maintain the pH during an assay. Illustrative buffers include borate, phosphate, carbonate, tris, barbital and the like. The particular buffer employed is not critical to this invention, but in an individual assay one or another buffer may be preferred.

Moderate temperatures are normally employed for carrying out the binding reactions of proteinaceous ligands and receptors in the assay and usually constant temperature, preferably, 25° to 40°, during the period of the measurement. Incubation temperatures for the binding reaction will normally range from about 5° to 45° C., usually from about 15° to 40° C., more usually 25° to 40° C. Where binding of nucleic acids occur in the assay, higher temperatures will frequently be used, usually 20° to 90°, more usually 35° to 75° C. Temperatures during measurements, that is, generation of singlet oxygen and light detection, will generally range from about 20° to 100°, more usually from about 25° to 50° C., more usually 25° to 40° C.

The concentration of analyte which may be assayed will generally vary from about $10^{-4}$ to below $10^{-16}$ M, more usually from about $10^{-6}$ to $10^{-14}$ M. Considerations, such as whether the assay is qualitative, semiquantitative or quantitative, the particular detection technique the concentration of the analyte of interest, and the maximum desired incubation times will normally determine the concentrations of the various reagents.

In competitives assays, while the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

The concentration of the sbp members will depend on the analyte concentration, the desired rate of binding, and the degree that the sbp members bind nonspecifically. Usually, the sbp members will be present in at least the lowest expected analyte concentration, preferably at least the highest analyte concentration expected, and for noncompetitive assays the concentrations may be 10 to $10^6$ times the highest analyte concentration but usually less than $10^{-4}$ M, preferably less than $10^{-6}$ M, frequently between $10^{-11}$ and $10^{-7}$ M. The amount of photosensitizer or chemiluminescent compound associated with a sbp member will usually be at least one molecule per sbp member and may be as high as $10^5$, usually at least $10-10^4$ when the photosensitizer or chemiluminescent molecule is incorporated in a particle.

While the order of addition may be varied widely, there will be certain preferences depending on the nature of the assay. The simplest order of addition is to add all the materials simultaneously. Alternatively, the reagents can be combined wholly or partially sequentially. When the assay is competitive, it will often be desirable to add the analyte analog after combining the sample and an sbp member capable of binding the analyte. Optionally, an incubation step may be involved after the reagents are combined, generally ranging from about 30 seconds to 6 hours, more usually from about 2 minutes to 1 hour before the sensitizer is caused to generate singlet oxygen and the light emission is measured.

In a particularly preferred order of addition, a first set of specific binding pair members that are complementary to and/or homologous with the analyte are combined with the analyte followed by the addition of specific binding pair members complementary to the first specific binding pair members, each associated with a different member of the group consisting of a photosensitizer and a chemiluminescent compound. The assay mixture, or a separated component thereof, is then irradiated and the light emission is measured.

In a homogeneous assay after all of the reagents have been combined, they can be incubated, if desired. Then, the combination is irradiated and the resulting light emitted is measured. The emitted light is related to the amount of the analyte in the sample tested. The amounts of the reagents of the invention employed in a homogeneous assay depend on the nature of the analyte. Generally, the homogeneous assay of the present invention exhibits an increased sensitivity over known assays such as the EMIT® (Supra Corporation) assay. This advantage results primarily because of the improved signal to noise ratio obtained in the present method.

The following assays are provided by way of illustration and not limitation to enable one skilled in the art to appreciate the scope of the present invention and to practice the invention without undue experimentation. It will be appreciated that the choice of analytes, photosensitizers, chemiluminescent compounds, surfaces, particles and reaction conditions will be suggested to those skilled in the art in view of the disclosure herein in the examples that follow.

In one embodiment of the invention the chemiluminescent compound 9-benzal-10-methylacridan, is covalently linked to an antibody for thyroid stimulating hormone (TSH) (Reagent 1). The 9-benzal-10-methylacridan, functionalized with a N-hydroxysuccinimidyl ester of a carboxyl group attached to the phenyl ring, reacts with the amino groups of the antibody. The linking group is a carboxamide. The photosensitizer utilized is rose bengal, which is covalently bound to latex particles having an average dimension of 0.5 micron. The latex particles and rose bengal are covalently bound to each other by means of chloromethyl groups on the latex to provide an ester linking group as described in *J. Am. Chem. Soc.*, 97: 3741 (1975). The latex particle is further linked to a second antibody for TSH by means of N-hydroxysuccinimidyl ester groups on the latex (Reagent 2). Both of the antibodies employed are monoclonal antibodies prepared by standard hybrid cell line technology. One antibody recognizes the α-subunit of TSH and the other recognizes the β-subunit of TSH. In conducting the assay a serum sample suspected of containing TSH is obtained from a patient. Fifty microliters of the sample is combined in a 500 μL aqueous medium, buffered with Tris buffer at pH 8.0, with Reagent 1 and Reagent 2 above. The amounts of Reagent 1 and Reagent 2 are sufficient to provide concentrations of each antibody of about $10^{-6}$ molar. The reaction mixture is then incubated for a period of one hour at 25° C. and then irradiated for 30 seconds with 560 nm light. The light intensity emitted following the irradiation is measured and the total light energy detected over a period of 30 seconds is compared with values obtained in a similar procedure with samples having known concentrations of TSH to determine the concentration of TSH in the unknown. Alternatively, following incubation, the latex particles are separated from the medium and placed in an aqueous buffered medium of pH 9.5, similarly irradiated, and the amount of light emitted from the system is measured as before.

In an alternative based on the above, Reagent 2 is rose bengal covalently linked to the second antibody and no latex particle is employed. In still another alternative approach based on the above, Reagent 2 is rose bengal covalently linked to the second antibody and Reagent 1 is 9-benzal-10-methylacridan covalently bound to latex particles, to which the first antibody is covalently attached. In still another alternative based on the above, Reagent 1 is as described immediately above, Reagent 2 is rose bengal covalently linked to latex particles, to which avidin is covalently attached, and a third reagent (Reagent 2A) that is the second antibody covalently linked to biotin is employed. Reagent 1 and the third reagent are combined with sample and incubated. Then, an excess of Reagent 2 is added and the remaining procedure is as described above.

In another alternative based on the above, a chloroperoxidase is substituted for the rose bengal. In this assay the irradiation step is replaced by addition of sodium bromide and hydrogen peroxide to produce singlet oxygen. Light emitted is measured as described above.

In another embodiment in accordance with the present invention, a first set of oil droplets (Reagent 3) is prepared from a solution of the photosensitizer, chlorophyll, in mineral oil in accordance with Giaever, supra. The oil droplets, which range from 0.1 to 2 microns in diameter, are functionalized and linked to a monoclonal antibody for human chronic gonadotropin (hCG). The chlorophyll is lipophilic and is therefore dissolved irreversibly in the lipophilic oil droplet. A second set of oil droplets (Reagent 4) is prepared in a similar manner. In this set of droplets the oil droplet is covalently linked to a second monoclonal antibody for hCG, which recognizes a different portion of the hCG molecule than that recognized by the first monoclonal antibody referred to above. 9-(Diphenylmethylidine)-N-methylacridan irreversibly dissolved in the lipophilic oil droplet by including a N,N-didodecylcarboxamide group bound to one of the phenyl groups of the acridan. The monoclonal antibodies are prepared by standard hybrid cell line technology. A urine sample suspected of containing hCG (50 microliters) is combined with excess quantities of Reagent 3 and Reagent 4 in an aqueous buffered medium (500 μL) at pH 7.5. The medium is incubated at 25° C. for a period of 20 minutes. The medium, without separation, is irradiated at 633 nm using a He/Ne laser for a period of one minute and the light emitted is measured as described above. The amount of light is compared with the amount emitted from samples containing known amounts of hCG and the amount of hCG in the unknown sample is determined by comparing the values. In this way a convenient and sensitive homogeneous immunoassay for hCG is conducted.

In an alternative approach based on the above, Reagent 3 has antibody for fluorescein in place of the antibody for hCG and an additional reagent (Reagent 3A) has the hCG antibody covalently linked to fluorescein. Reagent 4 has avidin in place of the second hCG antibody and a fourth reagent (Reagent 4A) has the second antibody covalently linked to biotin. In the assay Reagent 4A and Reagent 3A are combined with sample and incubated. Thereafter, Reagents 3 and 4 are added and incubated. The remainder of the above assay procedure is then carried out.

In another embodiment of the present invention, one set of liposomes (Reagent 5) (0.2 micron in diameter) is formed by high pressure extrusion of a phospholipid suspension in pH 7.4 buffer through a 0.2 micron pore membrane using a commercially available instrument designed for such purpose. A thyroxine analog is covalently linked to the liposome by first forming mercaptoacetamide groups on the liposome by reaction of phosphatidylethanolamine in the liposome with an active ester of methyl carboxymethyl disulfide followed by reaction with dithioerythritol. Bromoacetyl thyroxine is then allowed to react with the sulfhydrylated liposomes. A metallo-porphyrin dye is dissolved in the lipophilic portion of the liposome. Another set of liposomes (Reagent 6) is utilized to attach a monoclonal antibody for thyroxine. The antibody is attached covalently by means similar to the attachment of thyroxine. An enamine (2-dimethylaminomethylenepyran) is covalently linked by means of a carboxamide linking group to the surface of the liposome. Reagent 5 and Reagent 6 are combined in an aqueous buffered assay medium (500 μL) of pH 8.0 together with a serum sample suspected of containing thyroxine that contains anilinonaphthalene sulfonic acid to displace thyroxine from binding proteins (50 microliters) and accept energy from the oxygen-activated pyran to provide for long wave length emission. The assay medium is then incubated at room temperature for 1 hour. The medium is irradiated, without a separation step, at 650 nm for a period of 1 minute and the resulting emitted light is measured by means of a luminometer. The value obtained is compared with values obtained by conducting a similar assay with known amounts of thyroxine. In this way the amount of thyroxine in the serum sample is quantitated.

In an alternative approach based on the above, Reagent 6 has avidin in place of antibody for thyroxine. An additional reagent (Reagent 6A) has antibody for thyroxine covalently linked to biotin. Reagent 5 has antibody for fluorescein in place of thyroxine and an additional reagent (Reagent 5) has thyroxine linked covalently to fluorescein. In the assay Reagents 5A and 6A are combined with sample and incubated. Then, Reagent 5 and 6 are added, the mixture is incubated, and the remainder of the assay procedure is followed.

In another alternative based on the above, the metalloporphyrin dye is replaced by potassium molybdate that is incorporated into the aqueous phase of the liposomes. In this assay the irradiation step is replaced by addition of hydrogen peroxide to produce singlet oxygen. Light emitted is measured as described above.

In another embodiment 2-hydroxyethyl 9,10-dibromoanthracene is formed into a dye crystallite in a manner similar to that described by Gribnau. A monoclonal antibody that recognizes hepatitis B surface antigen is covalently attached to the dye crystallite by means of a carbamate linking group. A latex particle is treated to immobilize a second antibody for hepatitis B surface antigen by means of covalent attachment. The latex particle is further covalently linked to 9-(benzal-9H-xanthene) by means of an amide linking group. The dye crystallite has a particle size of on the average 2 microns and the latex particles have an average diameter of 0.2 microns. The monoclonal antibodies are prepared by standard hybrid cell line technology. A serum sample from a patient suspected of having hepatitis (50 μL) is combined in an aqueous assay medium (500 μL) at pH 7.0 with an excess of the dye crystallite and latex particles described above. The assay medium is then incubated at room temperature for a period of 30 minutes and then irradiated at 350 nm with a xenon light source for a period of 1 minute. The presence of hepatitis B surface antigen in the sample causes the dye crystallite and latex particles to come into close proximity by virtue of the immune binding of the respective antibodies with the antigen. Upon irradiation of the medium the 9,10-dibromoanthracene is excited and converts molecular oxygen to singlet oxygen. The singlet oxygen reacts with the xanthene to give a dioxetane, which spontaneously decays at room temperature to produce light. The light is measured photometrically and the amount of light over a certain threshold level indicates the presence of hepatitis B surface antigen in the sample. Irradiation of the medium is conducted at room temperature and the assay is conducted in a homogeneous manner to yield an assay for hepatitis B surface antigen.

Preferably, in this assay $Eu(TTA)_3$ is dissolved in the latex particles so as to cause the excited xanthene derivative to transfer its energy to the $Eu(TTA)_3$, which emits above 600 nm. This avoids serum interference that would otherwise occur because of absorption by serum components of light emitted directly from the xanthene luminescence.

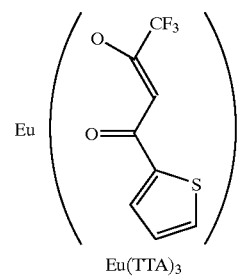

$Eu(TTA)_3$

In another embodiment the assay is for the determination of a particular blood group antigen on the surface of a red blood cell, namely, an A group antigen. Latex particles prepared as described above having a particle size of 150–500 nm are utilized. The latex particles have an antibody for the A group antigen covalently linked to the latex particle. The particles also have the enolether, 2-p-dimethylaminophenyl-3-phenyl-5,6-dihydrodioxene, dissolved in the latex. This latex particle reagent is combined in the aqueous medium (500 μl) with whole blood (100 μl) and 1×10$^{-4}$M photosensitizer, which is a hydrophobic photosensitizer, namely, phenazine-2-carboxylic acid. The hydrophobic dye intercalates into the red cells present in the sample. The medium is incubated at 25° C. for a period of 10 minutes and then irradiated at 400–450 nm with a tungsten source for a period of 30 seconds. The light emitted from the medium is measured and compared to the amount of light obtained in samples known to be free of A group antigen red blood cells. Thus, the amount of light over a threshold level indicates the presence of the A blood group antigen.

In another embodiment of the present invention the analyte is an HLA antigen on the surface of a cell. A sample (50 μL) suspected of containing the HLA antigen is combined in an aqueous assay medium (500 μL) buffered at pH 7.4. To the medium is also added an excess amount of a reagent which is an antibody for the HLA antigen covalently coupled to eosin by means of a thioether linking group. A chemiluminescent compound is also added to the assay medium. The chemiluminescent compound is chosen so that it will intercalate into the cell containing the HLA antigen. The chemiluminescent compound is an acridan, namely, 9-(dodecylphenylmethylidine-1-)N-(2-sulfonoxyethyl) acridan. The assay medium is incubated at room temperature for a period of 1 hour and then irradiated at 500–550 nm with a tungsten-halogen light source for a period of 1 minute. The light emitted from the assay medium is measured and the amount of light above a threshold level is indicative of the presence of the HLA antigen.

The present invention further encompasses compositions comprising a suspendible particle of 0.04 to 4000 nanometer average diameter comprising a chemiluminescent compound. The chemiluminescent compound may be covalently bound to the particle matrix or may be dissolved in the matrix or dissolved in a solvent that is dissolved in the matrix. The particles will preferably be polymeric or be oil droplets or vesicles such as liposomes. Where the particle is a liposome, the chemiluminescent compound will be associated with the lipid bilayer or dissolved in the aqueous interior of the liposome. The particle will have an spb member bound to it. Preferably, sbp bound particles will be 100 to 1000 μm in average diameter. Also encompassed are compositions comprised of two complementary sbp members bound to each other wherein one is associated with a photosensitizer and one is associated with a chemiluminescent compound.

Another aspect of the present invention relates to kits useful for conveniently performing an assay method of the invention for determining the presence or amount of an analyte in a sample suspected of containing the analyte. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit comprises (1) a composition comprising a suspendible particle comprising a chemiluminescent compound, the particle having an sbp member bound to it, and (2) a photosensitizer. The photosensitizer can be attached to an sbp member or it can be associated with a particle, to which an sbp member is bound. The kit can further include other separately packaged reagents for conducting an assay including ancillary reagents, and so forth.

Another embodiment of a kit in accordance with the present invention comprises in packaged combination a chemiluminescent compound associated with a first sbp member and a photosensitizer capable in its excited state of activating oxygen to its singlet state associated with a second sbp member.

EXAMPLES

The invention is demonstrated further by the following illustrative examples. Parts and percentages used herein are by weight unless otherwise specified. Temperatures are in degrees centigrade (° C.).

Abbreviations:

Ab$_F$—Mouse monoclonal antibody to fluorescein.

Ab$_{IF}$—Mouse monoclonal antibody to intrinsic factor.

B$_{12}$-LC$_{25}$-F—Vitamin B$_{12}$ linked to carboxy fluorescein (F) by means of a linking group 25 atoms in chain length, namely, HN(CH$_2$)$_6$NHCOCH$_2$OCH$_2$CONH(CH$_2$)$_6$NHCOCH$_2$NHCO BA-C$_{18}$—4-(N,N-Dioctadecylcarboxamidomethoxy) benzal acridan t-Bu—tert-butyl TFA—trifluoroacetic acid

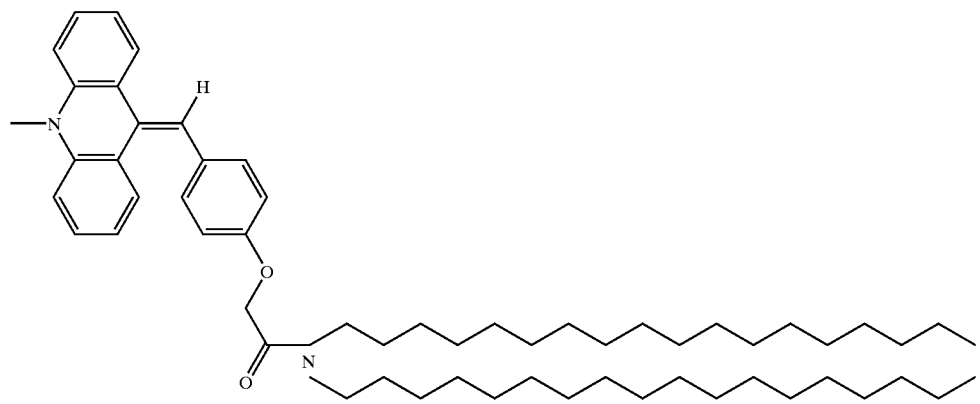

Biotin-LC$_{21}$-F

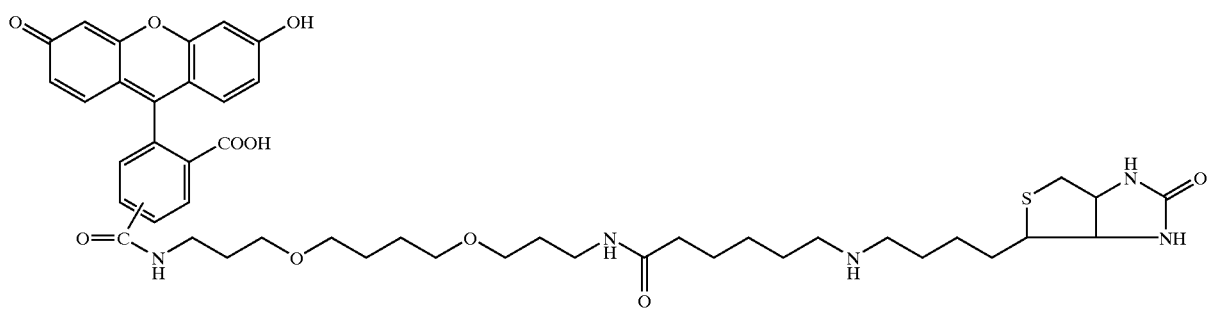

BSA—Bovine serum albumin
Chl-a—Chlorophyll-a

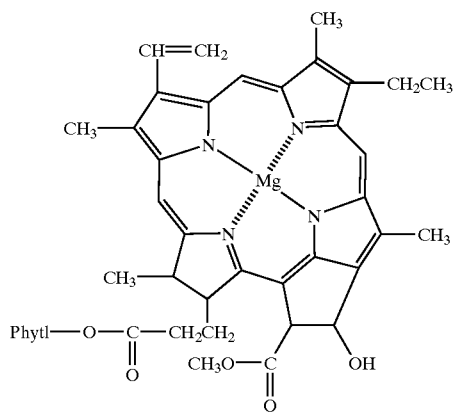

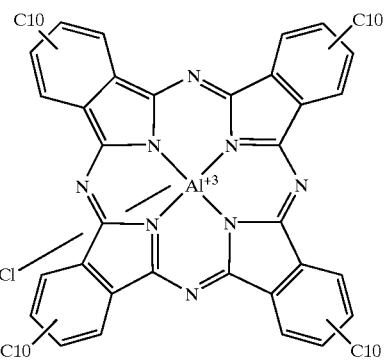

D-H$_2$O—dionized water
DPPC—dipalmitoylphosphatidyl choline
DPPG—dipalmitoylphosphatidyl glycerol
DPPE—dipalmitoylphosphatidyl ethanolamine
EDAC—1-Ethyl-3-(3-Dimethylaminopropyl) carbodiimide hydrochloride.

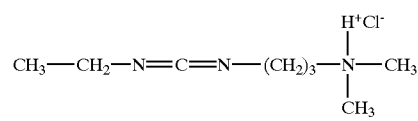

F—Fluorescein
F-NHS—the N-hydroxy succinimide ester of 6-carboxy fluorescein
F-LC$_{21}$NH$_2$—carboxyfluorescein to which is bound the linking group HN(CH$_2$)$_6$NHCOCH$_2$OCH$_2$CONH(CH$_2$)$_6$NH$_2$
HCG—Human chorionic gonadotropin
Lip—Liposome
nC$_{10}$—tetra-(n-decyl)phthalocyanin aluminum chloride complex.
OD—Oil droplet
OD/BA-C$_{18}$—Oil droplets containing BA-C$_{18}$
PB—Polystyrene beads
PB/BA-C$_{18}$—PB containing di-octadecylaminocarboxylbenzal acridan
PB/nC$_{10}$—PB containing tetra-(n-decyl)aluminum phthalocyanin
PBS—phosphate buffered saline 0.02M NaPi, 0.14 M NaCl/pH 7.2
Pi—Phosphate
Sulfo-NHS—Sulfo-N-hydroxysuccinamide
TSH—Thyroid stimulating hormone or thyrotropic hormone
SATA—S-acetylthioglycolic acid N-hydroxysuccinimide ester
RLU—Relative light units.
Ab$_1$ (αHCG)—monoclonal anti-HCGβ antibody 12A8
Ab$_2$ (βHCG)—monoclonal anti-HCGα antibody 9D7
Ab$_1$ (βTSH)—monoclonal anti-TSHβ antibody 35
Ab$_2$ (βTSH)—monoclonal anti-TSHβ antibody-9G3
NHS—N-hydroxysuccinimide
IF—intrinsic factor
DMSO—dimethyl sulfoxide
avidin-PB/BA-C$_{18}$—PB/BA-C$_{18}$ covalently bound to avidin
Ab$_F$-PB/nC$_{10}$—PB/nC$_{10}$ coated with Ab$_F$
DMF—dimethyl formamide
DCC—dicyclohexylcarbodiimide
TEA—triethylamine
TLC—thin layer chromatography
TNBSA—2,4,6-trinitrobenzenesulfonic acid Dig-CMO—O-carboxymethyloxime of digoxigenin-3-one
BGG—bovine gamma globulin
Biotin-$LC_7$-NHS—sulfosuccinimidyl-6-(biotinamido)-hexanoate All monoclonal antibodies were produced by standard hybrid cell technology. Briefly, the appropriate immunogen was injected into a host, usually a mouse or other suitable animal, and after a suitable period of time the spleen cells from the host were obtained. Alternatively, unsensitized cells from the host were isolated and directly sensitized with the immunogen in vitro. Hybrid cells were formed by fusing the above cells with an appropriate myeloma cell line and culturing the fused cells. The antibodies produced by the cultured hybrid cells were screened for their binding affinity to the particular antigen, e.g. TSH or HCG. A number of screening techniques were employed such as, for example, ELISA screens. Selected fusions were then recloned.

Example 1

Assay for Vitamin B12

Preparation of $B_{12}$-$L_{25}$-F Conjugate $B_{12}$-$LC_{25}$-F conjugate with a spacer arm of 25-atoms long (see below) was prepared by introducing carboxylic groups in the $B_{12}$ molecule by reacting with the $B_{12}$ molecule with methylisocyanatoacetate (which reacts with the hydroxyl group of ribose in the $B_{12}$ molecule forming a stable carbamate bond), followed by base hydrolysis of methyl ester to generate the carboxylic group. The introduced carboxylic group at the 5'-OH site was converted into the NHS ester of $B_{12}$ and then reacted with the fluorescein amine F-$LC_{21}$-$NH_2$ to generate the final product $B_{12}$-$LC_{25}$-F.

A. Synthetic scheme for 21 atom chain on 5-carboxy fluorescein.

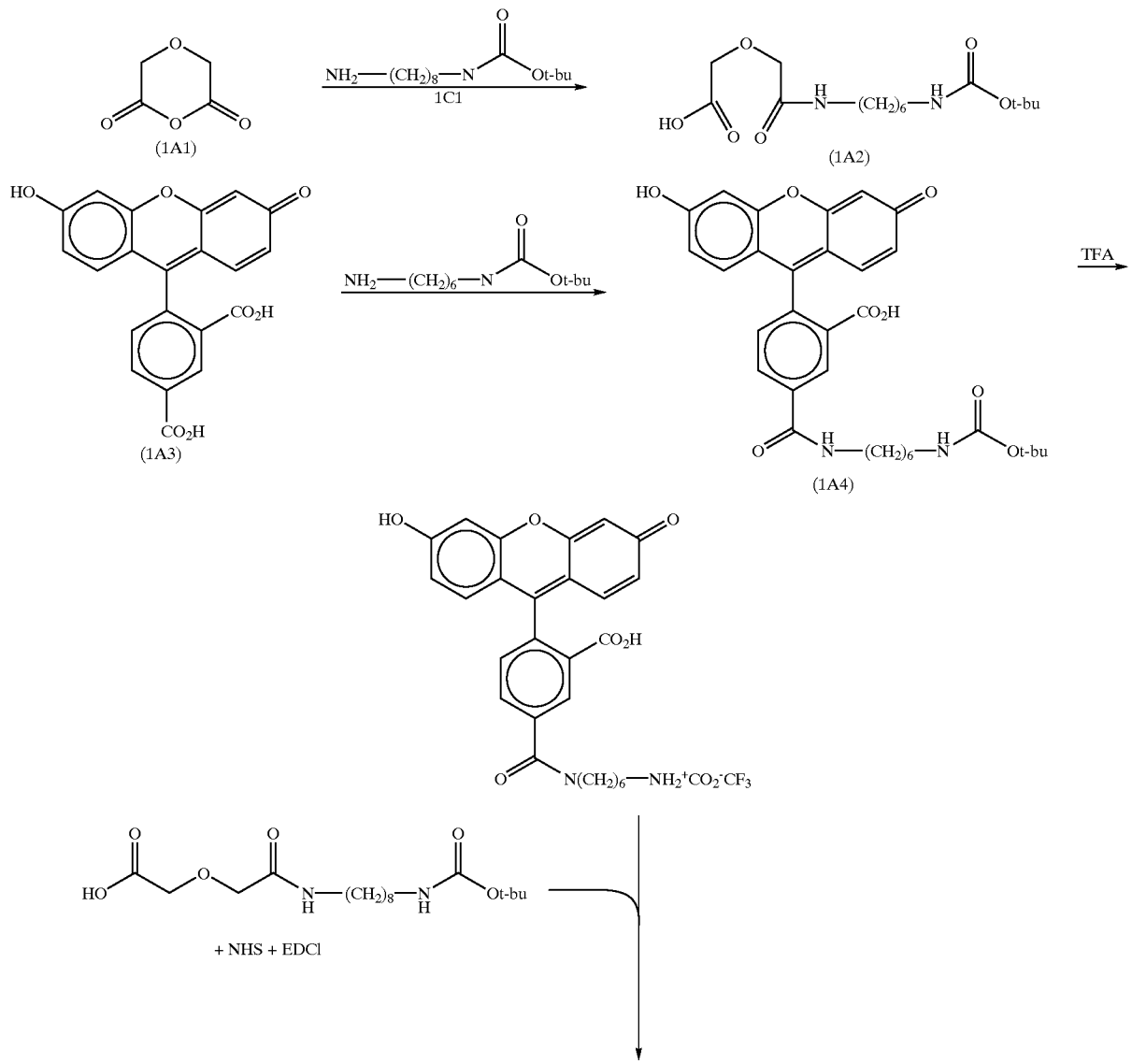

-continued

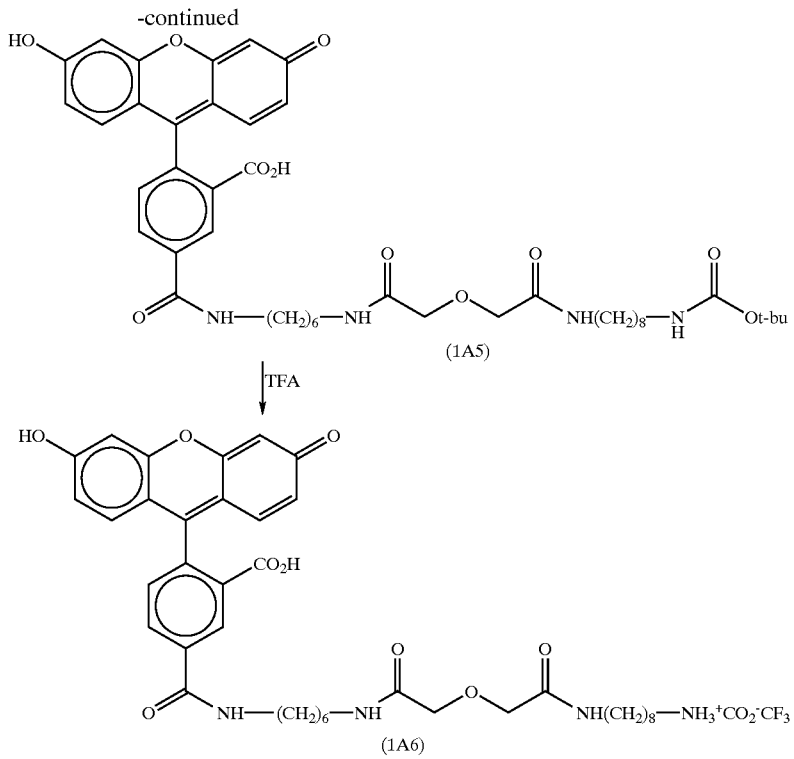

1.2 g (0.0056 mols) of the monoprotected diamine 1C1 was dissolved in 25 mL of anhydrous dichloromethane and to this stirring solution was added 0.64 g (0.0056 mols) diglycolic anhydride 1A1 and the reaction was left 5 hr at ambient temperature. The reaction mixture was concentrated and extracted with 50 mL water, 50 mL ethyl acetate. The organic phase was washed with 0.1N HCl (50 mL), water (2×50 mL) and dried with $MgSO_4$ and concentrated in vacuo to yield 1.35 g 1A2.

$^1$H NMR 100 MHz ($CD_3OD$) δ 4.0,3.85(2S,4,O—$CH_2$—CO) δ 3.0,2.82 (2t,4,$NCH_2$), δ 1.4 (S, $CH_3$)

500 mg (1.33 mmols) of 5-carboxyfluorescein, 1A3, (dried 80° over $P_2O_5$, in vacuo 0.05 mm, 16 hr.) was dissolved in 20 ml anhydrous dimethylformamide. To the stirring solution was added 280 mg (1.46 mmols) of 1-ethyl-3-dimethylaminopropylcarbodiimide and 168 mg (1.46 mmols) of N-hydroxysuccinimide. After stirring for 16 hr., 400 mg (1.85 mmols) of mono t-Boc 1,6-diaminohexane was added, and the mixture was stirred for an additional 4 hours at ambient temperature. The resulting mixture was concentrated to a thick solution and dissolved in 1:9 methanol-ethylacetate (100 mL) and extracted with water (3×50 ml), 0.1N HCl (100 ml). The organic phase was dried over $MgSO_4$ and evaporated in vacuo. The residue was purified on Analtech 1000 μ, 20×20 cm silica gel GF plates using 0.5% acetic acid and 10% methanol in dichloromethane. The pure bands were pooled and extracted with (1:1) methanol/dichloromethane, concentrated, and the residue was dissolved in the minimum of methanol and added dropwise into water. The mixture was then centrifuged and the solid dried in vacuo, yielding 83% of 1A4.

3.5 g (0.0064 mols) of mono tBoc 1,6-diaminohexyl-5-carbonyl fluorescein 1A4 (dried 90° C., over $P_2O_5$ in vacuo 0.05 mm 16 hr.) was treated with 40 ml dichloromethane/trifluoroacetic acid 1/1. The solution was swirled in an ice bath and after 5 minutes the solvent was evaporated and the crude residue was dried in vacuo overnight.

42 mg of mono-t-Boc 1,6-diaminohexylglycolic acid amide 1A2, 22 mg (0.190 mmols) N-hydroxysuccinimide, and 36.4 mg (0.190 mmols) 1-ethyl-3-(3-dimethylaminopropyl) carbodiimide were combined in 4 mL anhydrous dichloromethane and stirred at ambient temperature 16 hours. The solution of the activated acid was added dropwise into a stirring solution of 75 mg (0.127 mmols) of the above 1,6-diaminohexyl-5-carboxyl fluorescein derivative, 10 ml anhydrous dimethylformamide and 66 μl triethylamine. After 1 hour the reaction was taken up in water and extracted with ethyl acetate. The organic phase was washed with water (3×25 mL), dried with $MgSO_4$, concentrated and purified on one 20×20 cm 1000 μ Analtech silica gel GF plate 10% methanol, 0.5% acetic acid in dichloromethane. The pure band was isolated, extracted with methanol/dichloromethane, concentrated and dried in vacuo. The residue was taken up into 4 mL methanol and added dropwise to swirling 0.1N HCl (8 mL), centrifuged and dried, 84 mg 1A5, 84% yield.

$^1$H NMR 500 MHz($CD_3OD$) δ 8.4(d,1,ArH,J=0.71 Hz) δ 8.17 (dd,1,ArH,J=8.0 Hz) δ 7.3(d,1,ArH,J=8.0 Hz) δ 4.04 (d,4,O—$CH_2$—CO) δ 1.41 (S,9,3$CH_3$)

| | |
|---|---|
| Anal. Calc for $C_{42}H_{52}N_4O_{11}$: | C,63.7;H,6.8;N,7.0 |
| Found: | C,63.56;H,6.64;N,7.0 |

To the above tBoc-21-atom long chain amine of 5-carboxyfluorescein (dried 80° C. over $P_2O_5$ in vacuo, 0.05 mm) was added 5 ml trifluroacetic acid at ambient temperature. After 5 min the acid was evaporated and then dried 80° C. in vacuo to yield the etrifluoracetic acid salt 1A6.

FAB-MS $C_{37}H_{44}N_4O$ (M+H)$^+$ 689

B. Synthetic scheme for modification of $B_{12}$ at $0.5^1$ position of the ribose ring with a 25 atom spacer linked to 5-carboxyl fluorescein.

B. Synthetic scheme for modification of $B_{12}$ at $O^5$, position of the ribose ring with a 25 atom spacer linked to 5-carboxyl fluorescein

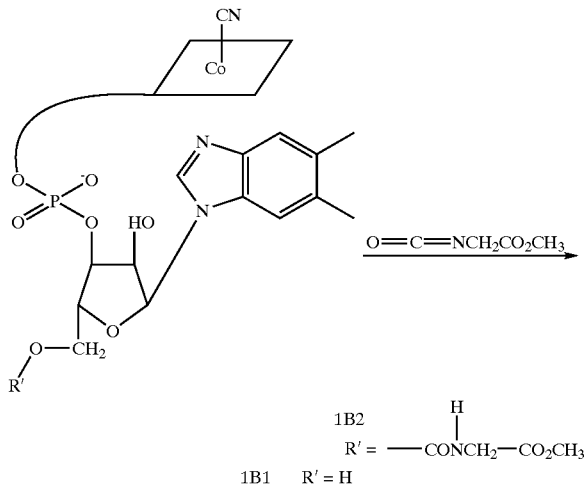

25 mg (0.0185 mmols) of vitamin $B_{12}$ (1B1) (dried 48 hours 80°, 10 μ) was dissolved in 1.25 ml anhydrous dimethylsulfoxide. To this stirring solution was added 21.2 mg (0.185 mmols) methyl isocyanatoacetate and reaction was then left 24 hours at ambient temperature. The reaction mixture was added dropwise into a 10 ml stirring ethylacetate solution. The precipitated product was centrifuged, then resuspended in a minimum amount methanol and reprecipitated. This material was purified on Whatman $PLC_{18}F$ preparative plate 1000 μ 20×20 cm eluant 2:8 isopropanol-water containing 0.5 ml acetic acid+1 g NaCl per 100 ml. Rf=0.625 Isolation from absorbant gave the methyl ester 1B2.

(+)-FABM5($C_{67}H_{93}CoN_{15}O_{17}P$)mw 1469.6; (M+H) 1470, (M-CN)$^+$ 1444

40 mg (0.0272 mmols) of the $B_{12}O^{5'}$-carbonyl glycine methyl ester 1B2 was taken up in 2.5 ml 2/1 methanol-water, pH adjusted to 9.5 with ammonium hydroxide and stirred for 16 hours at ambient temperature.

tlc analysis Whatman $KC_{18}F$;

2:8 isopropanol-water, 0.5% acetic acid, 1% NaCL; Rf≈0.79

The reaction mixture was concentrated to dryness and the product isolated using two Whatman $PLC_{18}F$ plates 1000 μ, 20×20 cm eluant same as above. The pure band was extracted with methanol, the extract was concentrated, dissolved in 2:7 methanol-dichloromethane, filtered and concentrated. The residue was dissolved in 4 ml methanol and added dropwise to 4 ml ethyl ether. The precipitate was centrifuged and dried at 60° C., over $P_2O_5$, 0.5 mm, 16 hours, to yield 28 mg product 1B3.

(+)-FAB-MS($C_{66}H_{91}CoN_{15}O_{17}P$) mw 1455.7, (M+H)$^+$ 1456, (M-CN)$^+$ 1431

15 mg (0.013 mmols) of $B_{12}O^{5'}$-carbonyl glycine 1B3, 3.66 mg (0.016 mmols) N,N-dicyclohexyl carbodiimide, 1.95 mg (0.017 mmols) N-hydroxy succinimide were combined with 5 ml anhydrous dimethyl formamide and stirred at ambient temperature for 16 hours. The reaction mixture was added dropwise to a stirring solution of 13.6 mg (0.17 mmols) 21-atom long chain amine of 5-carboxyfluorescein 1A6 in 2.02 mg (0.02 mmols) triethylamine in 4 ml dry dimethylformamide, and stirred 12 hours at ambient temperature.

The crude reaction was concentrated under vacuum at 40° C. and residue taken up in 2 ml methanol and precipitated with 6 ml ethyl ether and centrifuged. The solid was purified on Whatman $PLC_{18}F$ plate 1000 μ 20×20 cm, eluant 7:3 methanol-water, 0.5% acetic acid $_2$Rf~0.78, 37% yield 1B4.

(+)-FAB-MS ($C_{103}H_{133}CoN_{19}O_{25}P$), (M+H)$^+$ 2125; (M-CN)$^{21}$ UV/max 360 (ε 26,600), 50 (ε 57,000), 550(ε 9500).

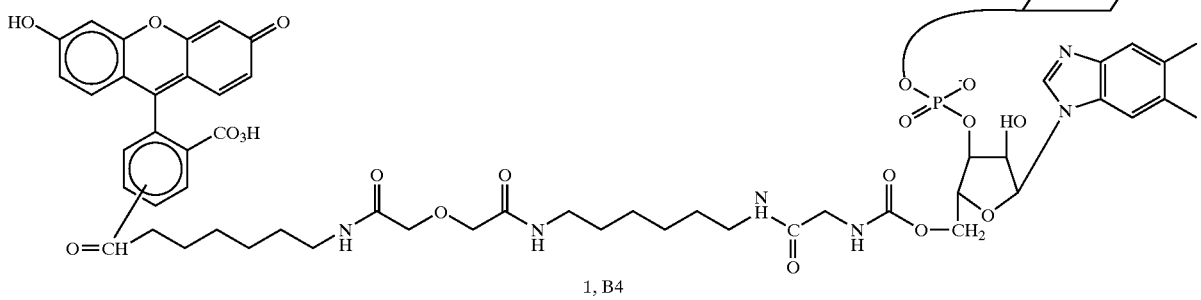

1, B4

II. Biotinylation of Anti-Intrinsic Factor ($Ab_{IF}$) Antibodies

The monoclonal anti-intrinsic factor antibodies ($Ab_{IF}$) were prepared by standard hybrid cell technology based on that reported by Kohler and Milstein in *Nature* 256(1975) 495–497.

Using biotin-$LC_7$-NHS from Pierce Chemical Co., Rockford, Ill., three different levels of biotinylations ($Ab_{IF}$:biotin in reaction mixture=1:10, 1:50, or 1:200) were performed. The $Ab_{IF}$ was in 0.05 M NaPi, 0.05 M NaCl/ pH=7.8 at [IgG]=2.5 mg/ml. To this solution DMSO (1% of the total volume) containing the required amount of biotin-$LC_7$-NHS was added and then the solution was incubated overnight at 4° C. Finally, the reaction mixtures were purified on SEPHADEX® G-25 (Pharmacia Biotech) and extensively dialyzed against 0.05 M NaPi, 0.02% $NaN_3$/ pH=7.2. The biotinylated anti-intrinsic factor antibodies were stored frozen.

III. Preparation of Particles

A. Materials 175 nm carboxylate modified latex: Bangs Laboratories, Inc. Carmel, Ind. 46032.

38 nm carboxylate modified latex: Duke Scientific Corporation, Palo Alto, Calif. 94303.

Ethylene glycol, benzyl alcohol, benzonitrile Aldrich Chemical Co.

SEPHADEX® G-25 (Pharmacia Biotech): Pharmacia.

$nC_{10}$: Ultra Diagnostics Corporation, Seattle, Wash. 98105.

B. $Ab_F$-PB/$nC_{10}$ 1. 38 nm diameter particles.

A 2.1 mM solution of $nC_{10}$ was prepared in benzyl alcohol. Ethylene glycol (16 mL) was placed in a 20 mL glass vial and warmed to 100° on a laboratory hot plate. Benzyl alcohol (1.6 mL) was added and the mixture stirred magnetically. Stock latex suspension (2 mL, 38 nm carboxylate modified latex containing 10% solids) was added and the mixture allowed to equilibrate for 3 to 4 minutes. The $nC_{10}$ solution (0.4 mL) was added slowly in 100 µL aliquots. Heating at 100° was continued for 5 minutes; then the mixture was allowed to cool to room temperature. After cooling, the mixture was applied to a column of SEPHADEX® G-25 (Pharmacia Biotech) (2.5×15 cm) equilibrated with 50% aqueous ethanol. The latex containing fractions were pooled and applied to a second SEPHADEX® G-25 (Pharmacia Biotech) column (2.5×35 cm) equilibrated with water. The latex was eluted in a volume of 30 mL.

2. 175 nm diameter particles.

A 2.1 mM solution of $nC_{10}$ was prepared in benzyl alcohol. Ethylene glycol (80 mL) was placed in a 125 mL Erlenmeyer flask and warmed to 110° on a laboratory hot plate. Benzyl alcohol (8 mL) was added and the mixture stirred magnetically. The $nC_{10}$ solution (2 mL) was added followed immediatley by stock latex suspension (10 mL, 175 nm carboxylate modified latex containing 10% solids). Heating was continued at 100° to 110° for 10 minutes while stirring vigorously. The flask was then placed in a room temperature water bath to cool. After cooling, the mixture was diluted with an equal volume of ethanol and immediately centrifuged at 15,000 rpm (Sorval, SA 600 rotor) for two hours. The faintly blue supernatant was decanted and the pellet resuspended in 50% aqueous ethanol (20 mL) using a bath sonicator to disperse the particles. Centrifugation was repeated, 15,000 rpm 1 hour. The supernatants were decanted and the pellet resuspended in water. Following a final centrifugation, the pellets were resuspended in water to a final volume of 20 mL.

3. Binding of the beads to $Ab_F$ is described in Example 3, paragraph V.

C. Avidin—PB/BA-$C_{18}$ 175 nm Diameter Particles.

A 10 mM solution of the dioctadecylbenzalacridan (BA-$C_{18}$) was prepared in benzonitrile. Ethylene glycol (80 mL) was placed in a 125 mL Erlenmeyer flask and warmed to 100° on a laboratory hot plate. Benzonitrile (9 mL) was added and the mixture stirred magnetically. The BA-$C_{18}$ solution (1 mL) was added followed immediately by stock latex suspension (10 mL, 175 nm latex containing 10% solids described above). Heating was continued at 100° for 5 minutes while stirring vigorously. The flask was then placed in a room temperature water bath to cool. After cooling, the mixture was diluted with an equal volume of 50% aqueous ethanol and immediately centrifuged at 15,000 rpm (Sorval, SA 600 rotor) for a total of 4 hours. The supernatant was decanted and the pellet resuspended in aqueous ethanol using a bath sonicator to disperse the particles. Centrifugation was repeated, 15,000 rpm 1 hour. The supernatants were decanted and the pellet resuspended in water. Following a final centrifugation, the pellets were resuspended in water to a final volume of 20 mL.

Binding of the beads to avidin is described in Example 3, paragraph VI.

IV. Assay Protocol

The assay was performed by mixing 100 µl of $B_{12}$ calibrators (diluted from an original 10 µg/ml $B_{12}$ stock solution 10 µM KCN) in assay buffer (0.05M KPi, 0.1% BSA, pH 7.5, BSA was free of $B_{12}$ and $B_{12}$ binder) with 50 µl of 2.2 ng/ml $B_{12}$-$LC_{25}$-F and 50 µl of premixed 88 ng/ml intrinsic factor (IF), 8.8 µg/ml $Ab_{IF}$-biotin. These mixtures were incubated at room temperature for 15 minutes in the dark; then 0.75 ml of 0.05 Tris-HCl, 0.05 NaPi, 0.15 M NaCl, 0.1% TRITON X-100® (Raymond Hans Company) pH 8.2 buffer containing $10^{10}$ beads Avidin-PB/BA-$C_{18}$ and $2.5 \times 10^{11}$ beads $Ab_F$-PB/$nC_{10}$ was added in each tube and the incubation was continued for additional 30 minutes by shaking in the dark at room temperature. Finally, each tube was illuminated for one minute using a halogen lamp fitted with a 650 nm cut off filter as light source, and then the chemiluminescent light was measured by integration for 20 sec using a Turner 20e luminometer. The results are summarized in FIG. 1.

Example 2

Assay for Digoxin

I. Preparation of $Ab_{Dig}$-Biotin

Anti-digoxin monoclonal antibodies ($Ab_{Dig}$) were prepared according to standard hybrid cell line technology and antibodies were purified by immobilized Protein A. Then the $Ab_{Dig}$-biotin was prepared by mixing the antibody (about 2–2.5 mg/mL in 0.05 M NaPi, 0.05 M NaCl/pH 7.8) and biotin-$LC_7$-NHS (Pierce Chemical Co., Rockford, Ill.) (first solubilized in DMF and a small aliquot used for the reaction) together and incubating for three hours at 4° C. In the reaction mixture, the molar ratio of the reactants was antibody:Biotin-$LC_7$-NHS=1:25. The uncoupled biotin was removed by SEPHADEX® G-25 (Pharmacia Biotech) column. The final conjugate was stored in 0.05 M NaPi, 0.001% Thimerosal/pH=7.4 at 4° C. or frozen.

II. Preparation of Dig-$LC_9$-F

This reagent was prepared in three successive steps by preparing (1) F-NHS, (2) F-$LC_9$-$NH_2$, and (3) Dig-$LC_9$-F.

A. Preparation of F-NHS. To 2 mL of 100 mg/mL 6-carboxyfluorescein and 30.6 mg/mL of NHS in DMF, 0.4 mL of 275 mg/mL DCC was added. The mixture was stirred overnight at room temperature in the dark. The formed dicyclohexylurea was removed by filtration. The formation of F-NHS was checked by TLC on silica plates, using $CH_2Cl_2$: methanol:acetic acid=85:15:1 solvent system.

DMF was removed by rotovap, and the product (F-NHS) was dried further under reduced pressure and stored desiccated at 4° C.

B. Preparation of F-LC$_9$-NH$_2$. To 1.5 mL of a solution of bis-(3-aminopropyl)-methylamine (LC$_9$) (Aldrich Chemical Co., Milwaukee, Wis.) in DMF was added, 1.2 mL of 125 mg/mL F-NHS in DMF followed by incubation at room temperature overnight with stirring in the dark. The molar ratio of F-NHS:LC$_9$ was 1:40. Then, the reaction mixture was diluted 1/20 with 0.5 M NaPi/pH 5.0, the pH of the mixture was adjusted to 5.0 by addition of phosphoric acid (1.0 M) and the whole mixture was loaded onto a (2.5×10 cm) of BioRex-70® column, equilibrated in 0.5 M NaPi/pH=5.0. After loading, the column was washed with the starting buffer until all of the bis-(3-aminopropyl) methyl amine was removed (monitored with TNBSA reaction). The column was washed with 0.001 M NaPi/pH=6.0 to remove the 6-carboxyfluorescein contaminant. Washing with low ionic strength buffer removed not only the 6-carboxyfluorescein but also another fluorescein containing contaminant, which has not been identified. Then, the column was washed with D-H$_2$O to remove the salts. Finally, the column was stripped with 0.8 M NH$_4$OH. The ammonium hydroxide was removed by lyophilization. After checking the purity, the product was stored desiccated at −20° C. The reaction was followed (and the purity of the product was checked) by paper electrophoresis (0.05 M NaPi/pH=5.8, 20 minutes using the paragon electrophoresis system) and by TLC (C$_{18}$ plates, using 50% methanol in D-H$_2$O as solvent).

C. Preparation of Dig-LC$_9$-F. A solution containing 23.05 mg (0.05 mmoles) of Dig-CMO prepared as described in U.S. Pat. No. 4,039,385, Example 2, the disclosure of which is incorporated herein by reference, 50.35 mg (0.1 mmoles) F-LC$_9$-NH$_2$ and 19.2 mg (0.1 mmoles) EDAC in 1.5 mL of DMF/DMSO (5:1) solvent was stirred overnight at room temperature in the dark. The Dig-LC$_9$-F and Dig-CMO (if any left unreacted) were precipitated out by adding 3 mL of D-H$_2$O, filtered out, and the solvent discarded. The filtered material was resolubilized in a solvent system consisting of CH$_2$Cl$_2$: methanol:acetic acid=60:40:5 and was loaded onto a (1.5×20 cm) silica gel column in the same solvent system. Under these conditions, Dig-CMO moved ahead of Dig-LC$_9$-F conjugate, and the F-LC$_9$-NH$_2$ remained bound to the top of the column. The purity of the material was checked by TLC silica gel plates, using the solvent system described above, and by electrophoresis on paper at pH=5.8. The solvents were removed from the purified material by rotovap, and the product was resolubilized into a minimum volume of methanol/DMF (70:30) and then centrifuged to remove the insoluble materials (silica gel). The last step was performed to remove most of the silica gel, which may be solubilized and co-eluted with the product during the purification. The product was stored in methanol/DMF (70:30) solvent system at −10° C. to −20° C. The concentration of the product was determined by A$_{490}$ from a standard curve constructed using known amounts of 6-carboxyfluorescein.

III. Assay Protocol

Figure 2:
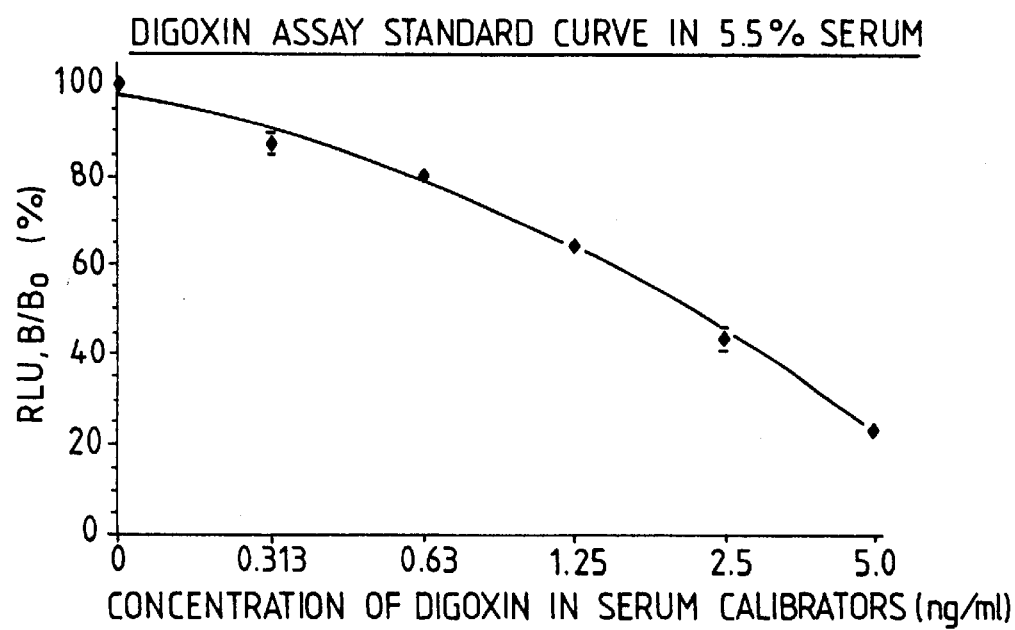
FIG. 2 is a graphic depiction of the results of an assay for digoxin.

The assay was performed by mixing 50 μl of digoxin calibrators in serum (human TSH free normal serum) with 50 μl of 1.74 ng/ml Digoxin-LC$_9$-F conjugate in assay buffer (0.05 M Tris-HCl, 0.05 M NaPi, 0.15 M NaCl, 2 mg/ml BSA, 0.2 mg/ml BGG/pH 8.2) and 50 μl of 160 ng/ml Ab$_{Dig}$-biotin in the same buffer as above. These mixtures were incubated at room temperature for 15 minutes, then 0.75 ml of 0.05 M Tris HCl, 0.05 M NaPi, 0.15 M NaCl/pH 8.2 buffer containing 10$^{10}$ acceptor beads (Avidin-PB/BA-C$_{18}$) and 2.5×10$^{11}$ sensitizing beads (Ab$_F$-PB/nC$_{10}$) was added in each tube and the incubation was continued for additional 30 minutes by shaking in dark at room temperature. Finally, each tube was illuminated for one minute using a halogen lamp fitted with 650 nm cut off filter as light source and then the chemiluminescent light was measured for 20 seconds integration using a Turner 20e luminometer. The results are summarized in FIG. 2.

Example 3

Assay for Human Chorionic Gonadotropin and Assay for Thyroid Stimulating Hormone I. Reagents and Materials A. The p-(N,N-dioctadecylcarboxamidomethoxy)benzal acridan (BA-C$_{18}$) was synthesized by the following procedure:

All reagents were obtained from Aldrich Chemical Co., except as indicated.

1. p-Formylphenoxyacetic Acid Dioctadecylamide

To a 100 mL solution of freshly distilled tetrahydrofuran (THF) was added p-formylphenoxyacetic acid (K & K Labs) (MW 180, 0.540 g, 3.0 mmol), triethyl amine (MW 101.19, 0.333 g, 3.3 mmol) and trimethylacetyl chloride (MW 120.57, 0.398 g, 3.3 mmol). After 20 minutes of heating at reflux, dioctadecylamine (Fluke) (MW 522.01, 1.723 g, 3.3 mmol) was added. The reaction was refluxed overnight.

The following day, the reaction mixture was diluted with water and extracted from the reaction solution with methylene chloride. The methylene chloride extracts were dried over sodium sulfate.

2. p-(N,N-Dioctadecylcarboxamidomethoxy)benzal-9-methylacridan

To 10-dimethoxyphosphinyl-9-methyl acridan (Monatshi Chem. 114 3 (1988) (MW 303.27, 0.100 g, 3.3 mmol) in anhydrous THF was added 0.413 mL of 1.6 M n-butyl lithium solution in hexane at −78° C. (acetone/dry ice bath) under argon. Upon the addition of the n-butyl lithium solution, the solution appeared yellow. A solution of the above amide in THF was added 20 minutes after the addition of n-butyl lithium. The reaction solution was permitted to warm to room temperature overnight.

The following day the product was isolated by TLC (Silica gel-3:7-ethylacetate/hexane). The isolated product was analyzed by mass spectrum analysis and NMR and stored in the dark.

B. Singlet oxygen generator dye (nC$_{10}$) was from ULTRA diagnostic Corporation. EDAC, SATA, hCG, and BSA were from Sigma Co. The Ab$_1$(αTSH)-biotin and Ab$_2$(αHCG)-biotin and the Ab$_2$(αTSH)-F were prepared by procedures similar to those described in Example 1, paragraph II (see also U.S. patent application Ser. No. 07/389,659 filed Aug. 4, 1989, the relevant portions of which are incorporated herein by reference).

A luminometer from Turner Designs (model 20e) was used.

II. Preparation of Oil Droplets Stabilized with Anti-HCG Antibody (Ab$_1$($\alpha$HCG)-OD/BA-C$_{18}$)

The anti-HCG antibody labeled oil droplets (OD) were prepared by transferring 1 ml of 10 mg/ml anti-HCG-$\beta$ (12A8, IgG) in a glass tube containing 50 $\mu$l of 5 mM dioctadecylbenzal acridan (BA-C$_{18}$) in dibutyl phthalate. The protein was in 0.05 M NaPi, 0.15M NaCl/pH 7.6. The oil was emulsified by sonication and simultaneous continuous mechanical mixing. It should be noted that high energy sonicators were required for preparing smaller oil droplets. The sonication was performed for 7 minutes using Bronson sonicator (running water at room temperature was used as coolant). The unbound protein was removed by adding 25% Na$_2$SO$_4$ solution to get 8% to 9% final concentration and then centrifuging (microfuge, setting 8 for 10 min.). The washing step was performed three times (the centrifugation speed should be adjusted such that the oil droplets are separated but do not coalesce). After the final wash the particles were suspended in 1 ml of 0.05 M NaPi, 0.15 NaCl, 4 mg/ml BSA/pH7.6 and sonicated again for three minutes. The final volume of the preparation was adjusted to 5 ml and sucrose was added to 2% final concentration. These Ab$_1$ ($\alpha$HCG)-OD/BA-C$_{18}$ particles were stored at 4° C. The oil droplets prepared by the method described above were heterogenous in size with a average diameter of 1–5 $\mu$.

III. Preparation of Avidin-Lip/nC$_{10}$

The liposomes were prepared by methanol dilution method. Typically a mixture of lipids: Cholesterol (2.0 mg), DPPC (Avanti Polar Lipids, Alabaster, Ala.) (23.8), DPPG (Avanti Polar Lipids, Alabaster, Ala.) (6.5 mg), maleimide-DPPE (Molecular Probe, Eugene, Oreg.) (0.5 mg) and nC$_{10}$ (0.5 mg were dissolved in warm methanol (200 $\mu$l ) and then added into 2 ml of vortexing buffer-B (0.05 m NaPi, 0.05M NaCl, 5 mM EDTA/pH 6.0). The suspension then was passed through a (1.5×20 cm) Sephadex G-25 column in buffer-B. The pooled liposome containing fractions were centrifuged by microfuge to remove any large particles, when necessary. Finally, the maleimide-containing liposomes were slowly added into stirred succinylated avidin-SH (prepared as described below) solution in buffer-B. After flushing with argon this mixture was mixed gently (no stirring bar) overnight at 4° C. The excess maleimide groups were blocked with 2 mM mercaptosuccinic acid (in reaction volume) for 30 min. at 4° C. followed by the addition of iodoacetic acid to a final 5 mM concentration to block the excess thiol groups (30 min at 4° C.). The reaction mixture was then concentrated to 2.5–3 ml by means of a CENTRIPREP-30® (W.R Grace Company) device and the uncoupled avidin molecules were removed by gel filtration on a (1.5×50 cm) SEPHAROSE-2B® (Pharmacia Biotech) column in buffer-B.

IV. Preparation of Succinylated Avidin-SH

Avidin was reacted with SATA (5 moles per mole of avidin) (10 mg/ml avidin in 1M NaPi/pH7.4) overnight at 4° C. To the same solution succinic anhydride in DMF (50 moles per mole of avidin) was added (total DMF was less than 1% of the reaction volume), and the solution was incubated for 2 hours. The pH of the reaction mixture was kept at 7.4 by addition of 0.5M Na$_2$HPO$_4$. The protected thiol groups (thioester) were liberated with hydroxylamine (0.1M, at pH 7.0) for 1 hour at room temperature. Finally, the excess small molecular weight molecules were removed by use of a 1.5×30 cm G-25 column in buffer-B (0.05 M NaPi, 0.05 M NaCl, 5 mM EDTA/pH6.0, degased and argon saturated). The protein peak (avidin-SH) was collected and the protein was reacted with maleimide containing liposomes.

V. Preparation of Anti-Fluorescein Coated nC$_{10}$-stained Beads (AbF-PB/nC$_{10}$rboxylated polystyrene beads (38 nm)

(see Example 1, paragraph IIIB) were stained with nC$_{10}$. EDAC/sulfo-NHS conjugation chemistry was used to couple the Ab$_F$ to these polystyrene beads. Typically, 10 ml of 0.02 M NaPi containing 5 mg/ml nC$_{10}$ stained carboxylated polystyrene beads and 11 mg/ml sulfo-NHS (pH adjusted to 5.5) was mixed with 1 ml of freshly prepared solution of EDAC (200 mg/ml) in D-H$_2$O. After incubating at room temperature (in the dark) for 25 minutes, the beads were centrifuged to remove the excess EDAC (since EDAC causes microaggregation of these beads, it was possible to pellet them with conventional centrifuges, e.g., Sorval using SA-600 rotor at 15000 rpm). The pelleted beads were resuspended in 3 ml of 0.005 M NaPi/pH5.8 and then transferred into a stirred protein solution (15 m of 0.02 M Borax, 0.08 M NaCl, 2 mg/ml 3Gl IgG (Ab$_F$), 8 mg/ml BSA/pH 8.9). The mixture was gently shaken (no stirring) overnight at 4° C. The remaining reactive groups on the beads, if any, were blocked with 0.083 M glycine and 15 mg/ml BSA/pH8.9 at 4° C. for 60 minutes. The uncoupled proteins were removed by successive washing with 0.05 M NaPi, 0.15 M NaCl/pH7.6,. The final pellet was resuspended in the washing buffer, sonicated, and stored as is at 4° C. The final size of these beads was 140 nm.

VI. Preparation of Avidin-Coated and Benzal Acridan-Stained beads (Avidin-PB/BA-C$_{18}$)

Carboxylated latex beads (0.175 $\mu$) were stained with the BA-C$_{18}$. (See Example 1, paragraph IIIC.) EDAC/sulfo-NHS conjugation chemistry was employed for conjugating the avidin to these particles. The activation of the beads by sulfo-NHS/EDAC was performed in the same way as it was described for Ab$_F$-PB/nC$_{10}$ preparation above. The activated beads (100 mg) were centrifuged to remove excess EDAC, then resuspended in 2.5 ml of 0.005 M NaPi/pH 5.8 and transferred into a stirred avidin solution (15 ml of 0.025 M Borax, 1.33 mg/ml avidin/pH9.1). The mixture then was mixed gently at 4° C. overnight. The avidin on the beads was succinylated by adding 20 ul of 1 M succinic anhydride in DMF (60-fold molar excess over avidin) and incubating further at 4° C. for 1 hour. The beads were blocked with 7 mg/ml BSA (the final concentration in the reaction mixture) for 60 min. at 4° C. Finally the beads were washed three times with 0.05 M NaPi, 0.15 M NaCl/pH7.6 by centrifugation and stored in 10 ml of washing buffer. In the last step the beads were sonicated to obtain monodispersed particles. The size of the beads did not change significantly after protein labeling (~190 nm). The Avidin-PB/BA-$C_{18}$ was stored in washing buffer at 4° C.

VII. Preparation of Biotin-$LC_{21}$-F
1. Reaction Scheme

Ag-MP-1 (Cl⁻) anion exchange resin, BioRad Laboratories.
3. Fluorescein Amine Hydrochloride VII3.

6-Carboxy fluorescein (VII 1) (10 g, 26.6 mmole) was dissolved in dry DMF (25 ml). N-hydroxysuccinimide (3.22 g, 28 mmole) was added as a solid to the DMF solution and

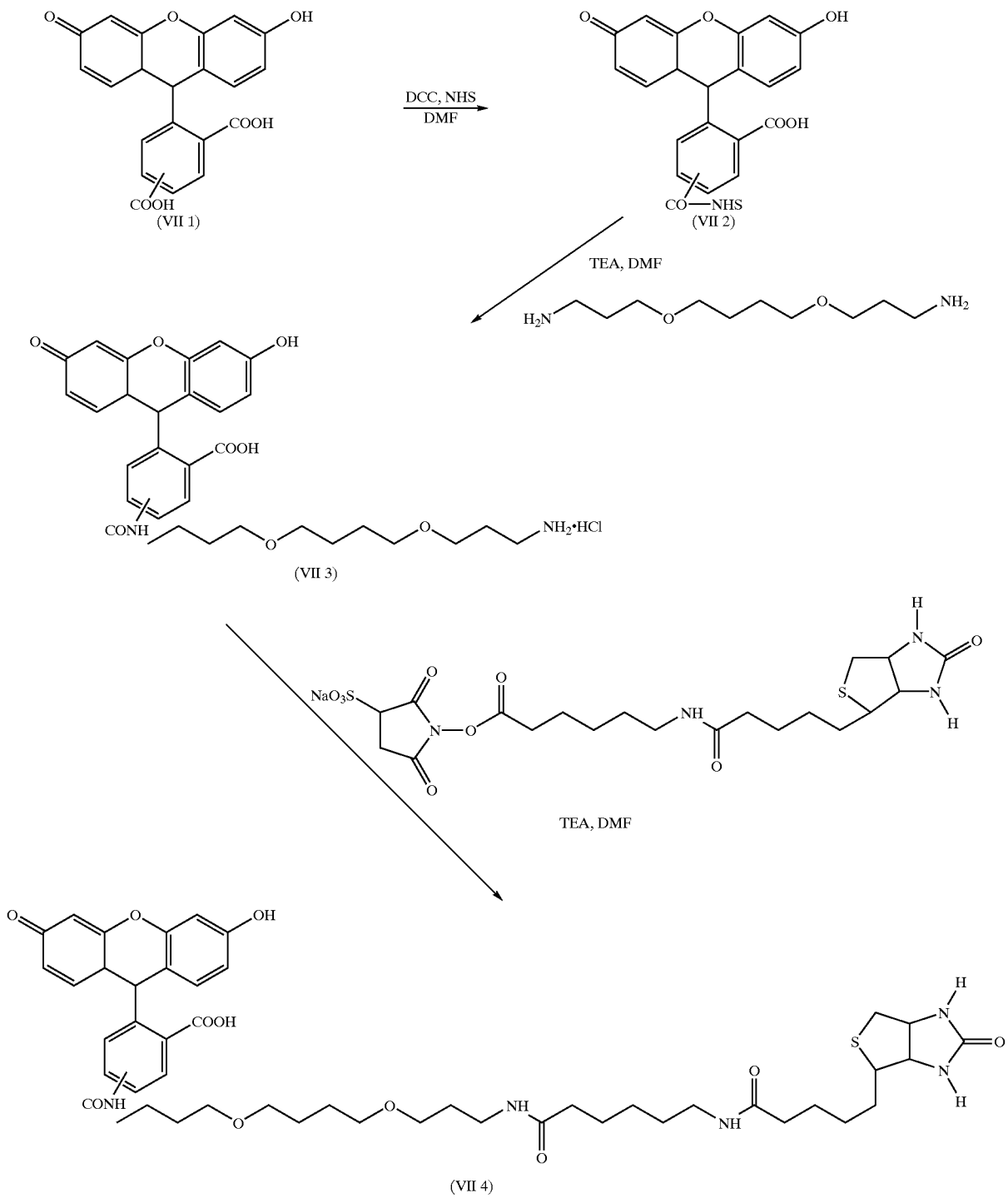

2. Materials 6-carboxyfluorescein, Kodak; biotin-NHS ester, Pierce Chemical Co.; 4,9-dioxa-1,12-dodecane diamine, Aldrich Chemical Co.; dry DMF distilled from calcium oxide;

allowed to dissolve. The mixture was then cooled in an ice bath. Dicyclohexyl carbodiimide (5.8 g, 28 mmole) was dissolved in dry DMF (10 ml) and added all at once to the cold DMF solution. The mixture was stirred at ice bath temperature for 30 min. and then allowed to come to room temperature. The course of the reaction was followed by tlc (10% MeOH-CH$_2$Cl$_2$ containing 1% acetic acid). After 3 hours, formation of the fluorescein NHS ester VII2 was complete. 4,9-Dioxa-1,12-dodecane diamine (25.5 g, 125 mmole) was diluted with dry DMF (10 ml). The fluorescein NHS ester reaction mixture was cooled in ice under an argon atmosphere and the diamine solution added dropwise over a period of 5 minutes. The cooling bath was removed and stirring was continued at room temperature. The course of the reaction was followed by tlc using the above system. When the reaction was judged complete, the mixture was diluted with water (100 ml) and cooled in ice to precipitate dicyclohexylurea which was removed by filtration.

The filtrate was slurried with AG-MP-1(Cl$^-$) anion exchange resin and poured into a chromatography column. The resin was washed with 50% aqueous methanol until free diamine could no longer be detected by ninhydrin. The resin was then eluted with 0.1 N hydrochloric acid in 50% aqueous methanol. Fluorescein amine hydrochloride eluted first followed by 6-carboxy-fluorescein. Pure fractions were pooled and taken to dryness on the rotovap. After drying under high vacuum 3.4 g of pure fluorescein amine hydrochloride VII3 was recovered.

4. Fluorescein-LC$_{21}$-biotin VII 4.

Fluorescein amine hydrochloride VII3 (350 mg, 0.61 mmole) was dissolved in dry DMF (15 ml). Triethylamine (300 µl) was added followed by biotin NHS ester (445 mg, 0.8 mmole). The course of the reaction was followed by tlc (MeOH-CH$_2$Cl$_2$-acetic acid-water, 20:78:1:1). When the reaction was judged complete, DMF was removed on the rotovap. The residue was dissolved in methanol (10 ml) and slurried with silica gel (10 g). The slurry was dried on the rotovap to a free flowing powder which was slurried in dichloromethane and applied to the top of a silica gel column (2.5×25 cm) equilibrated with dichloromethane. The column was eluted with the above tlc solvent mixture. Fractions containing product were pooled and solvent removed on the rotovap. The residue was taken up in ethanol and filtered. The filtrate was slowly evaporated and the product was deposited as a gum. The gum was dried under high vacuum to give 350 mg of fluorescein-LC$_{21}$-biotin VII 4 (F-LC$_{21}$-biotin) which was used without further characterization.

VIII. Assays

A. HCG Assay Standard Curve (OD with Lip)

An HCG assay was performed by first mixing HCG (varying amounts), Ab$_1$(αHCG)-OD/BA-C$_{18}$ and Ab$_2$(αHCG)-biotin together. After incubation at room temperature for 1 hour, excess amount of Avidin-Lip/nC$_{10}$ was added and the incubation continued at room temperature for an additional 30 minutes. Finally, the tubes were illuminated for 1 minute each and the luminescence measured for 20 seconds.

Protocol:
Combine:
50 µl of HCG at varying conc. in sample buffer, (0.05 M NaPi, 0.15 M NaCl, 04% BSA, 20% sucrose 4 mg/ml dextran sulfate (T-500) pH 7.5)
50 µl of 4 µg/ml Ab$_2$(αHCG)-biotin in assay buffer (0.05 M NaPi, 0.15 M NaCl, 0.4% BSA, pH 7.5), and
50 µl of Ab$_1$(αHCG)-OD/BA-C$_{18}$ reagent (5×10$^8$OD/tube)
Incubate 1 hr at room temperature with shaking in the dark
Add:
50 µl of 1.5×10$^{12}$ Avidin-nC$_{10}$ Lip (7.3×10$^{10}$ lip/tube)
Incubate 30 min. at room temperature with shaking in the dark.

Figure 3:
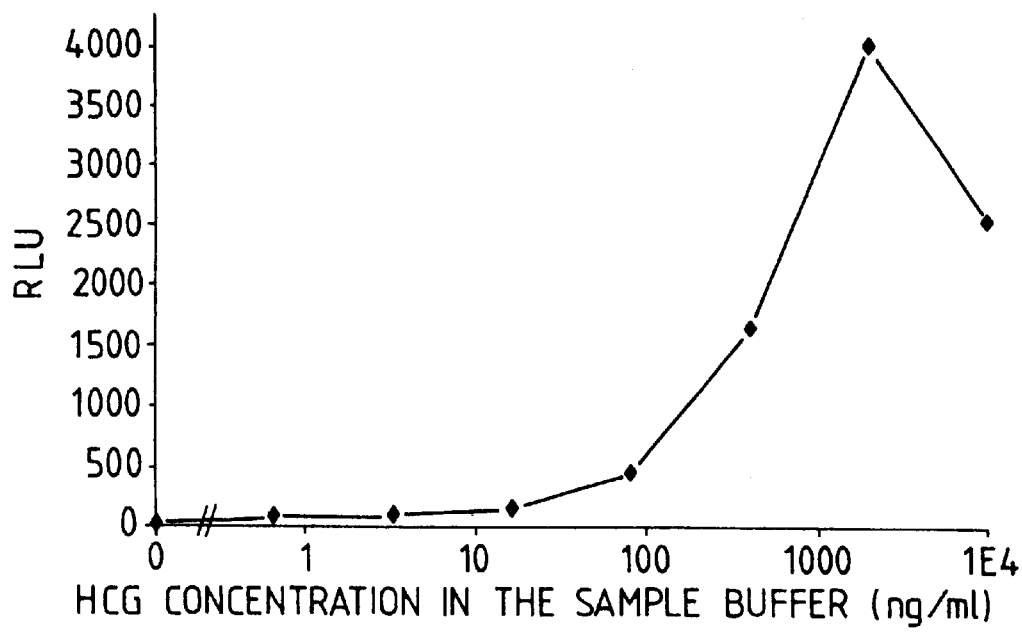
FIG. 3 is a graphic depiction of the results of an assay for HCG in accordance with the present invention.

Illuminate for 1 min. with a halogen lamp (120 mW light output when using a 650 nm cut-off filter). Then, with light source off, measure emitted light intensity for 20 seconds. The results are summarized in FIG. 3.

B. Assay of Biotin-LC$_{21}$-F.

Figure 4:
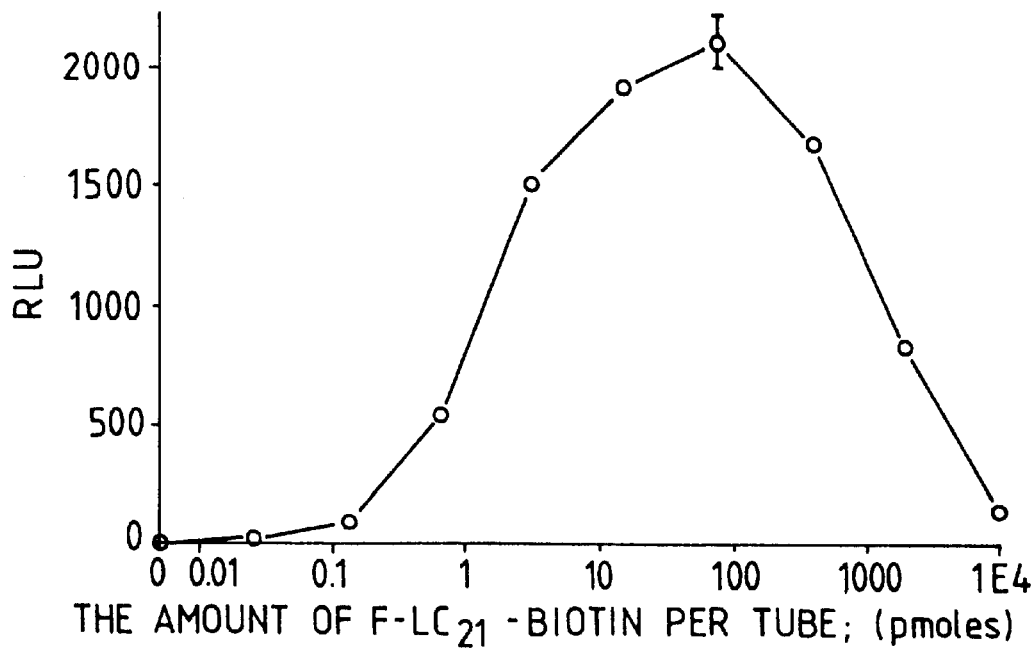
FIG. 4 is a graphic depiction of the results of a test in accordance with the present invention.

The test was performed by mixing 50 µL of avidin-PB/BA-C$_{18}$ (2×10$^{11}$ beads/ml), 50 µL of AbF-PB/nC$_{10}$ (5×10$^{12}$ beads/ml) and 100 µL of biotin-LC$_{21}$-F (varying amounts) in 0.05 NaPi, 0.15 M NaCl, 4 mg/ml BSA/pH 7.6. This mixture was incubated at room temperature for 1.5 hours with shaking in the dark. Finally, each tube was illuminated with halogen lamp source (fitted with 650 nm cut off filter) for 1 minute after which the light output was measured for 20 seconds by integration of the light intensity in a Turner 20e luminometer. The results are summarized in FIG. 4.

C. TSH Assay Standard Curve

Figure 5:
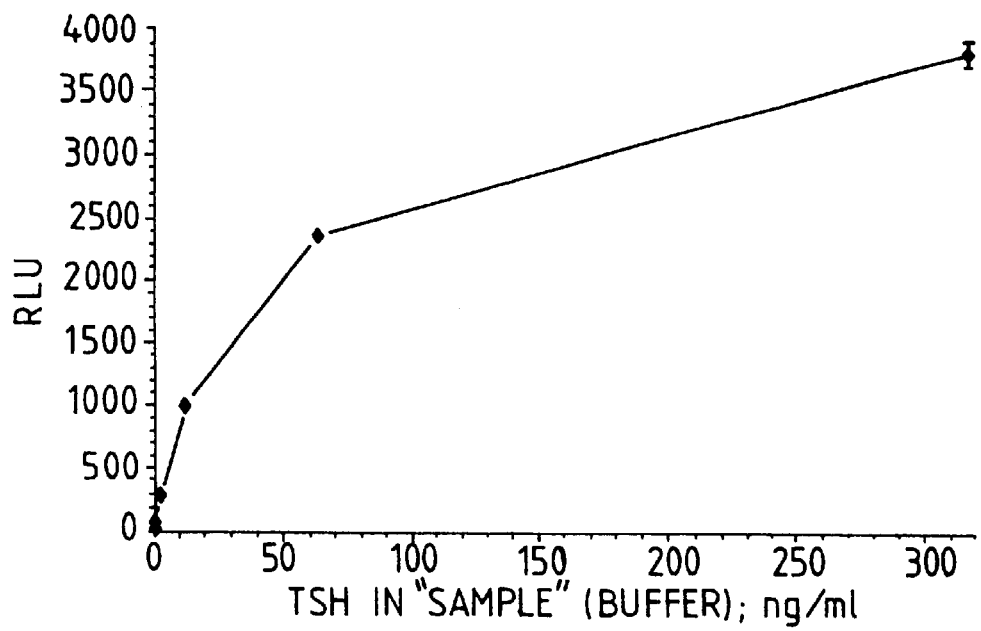
FIG. 5 is a graphic depiction of the results of an assay for TSH in accordance with the present invention.
Figure 6:
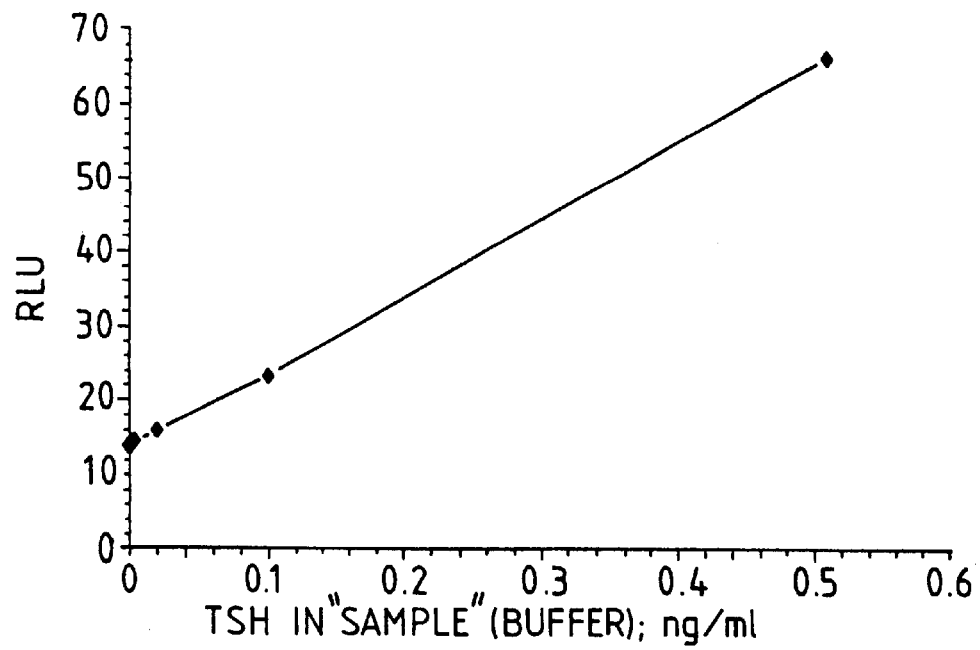
FIG. 6 is a portion of the graphic depiction of FIG. 5.

The TSH assay was performed by mixing 200 µL of TSH at varying concentrations in 0.05 m NaPi, 0.15 m NaCl, 4 mg/ml BSA/pH 7.6 with 50 µL of 4 µg/ml Ab$_1$(αTSH)-biotin and 4 µg/ml Ab$_2$(αTSH)-F. These mixtures were incubated at room temperature for 1.5 hours. Then, 100 µL of PBS containing 10$^{10}$ Avidin-PB/BA-C$_{18}$ beads and 2.5× 10$^{11}$ Ab$_F$-PB/nC$_{10}$ beads were added into each tube. The incubation was continued at room temperature for another 1.5 hours. Finally, each tube was illuminated with a halogen lamp source (fitted with 650 nm cut off filter) after which the light output was measured by integrating the light intensity for 20 seconds (FIG. 5 and FIG. 6) in a Turner 20e luminometer.

Example 4

Assay for HCG Using Soluble Photosensitizer and Acceptor Oil Droplets

I. Reagents:

Acceptor dye stained oil droplets=Ab$_1$(αHCG)-OD/BA-C$_{18}$ (described in Example 3, Part II).

Ab$_2$(αHCG)-biotin—prepared similarly to Example 2, Part I, from the NHS derivative of biotin purchased from Pierce Chemical Co.

Strepavidin-T680—from Ultralite Diagnosties Co., strepavidin labeled with water soluble analog of the nC$_{10}$ dye described above.

II. Assay

Figure 7:
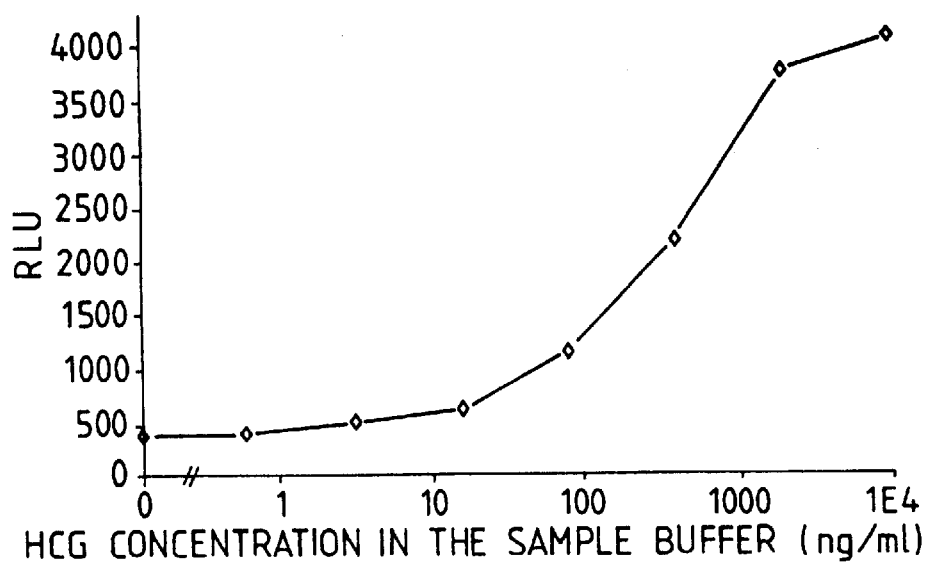
FIG. 7 is a graphic depiction of the results of another assay for HCG in accordance with the present invention.

The assay was performed by mixing 50 µl of sample buffer (0.05 M NaPi, 0.15 M NaCl, 4 mg/ml BSA, 4 mg/ml Dextran-SO$_4$ (T500), 20% sucrose/pH 7.6) containing varying amounts of HCG with 50 µl of 4µg/ml αHCG$_2$-biotin in assay buffer (0.05 M NaPi, 0.15 M NaCl, 4 mg/ml BSA/pH 7.6) and 50 µl Ab(αHCG)-OD/BA-C$_{18}$ reagent containing 5×10$^8$ oil droplets. This mixture was incubated for one hour at room temperature in the dark. Then, 50 µl of 2 µg/ml Strepavidin-T680 in assay buffer was added in each tube and the incubation continued for additional 30 minutes. Finally, each tube was illuminated for 1 minute with a halogen lamp light source (fitted with 650 nm cut off filter) and then the light output was measured for 20 seconds using the Turner's 20e luminometer. The results are summarized in FIG. 7.

Example 5

Homogeneous Assay for Target Oligonucleotide

The target sequence was selected from the *Escherichia coli* K12 DNAJ gene (J. C. A. Bardwell, K. Tilly, E Craig, J. King, M. Zylicz, and C. Georgopoulos, *J. Biol. Chem.* 261; 1782–1785 (1986)). A 50 mer with the sequence shown was prepared by the phosphite triester approach using a Biosearch 8750, including a biotin incorporated at the 5'-end using Biotin-ON™ Phosphoramidite (Clontech, Palo Alto, Calif.).

Sequence:
GCGGGCGAAGGTGAAGCGGGCGAGCATG-GCGCACCGGCAGGCGATCTGTA. The probe was a complementary 30 mer including a fluorescein (F) attached to a modified C, having the sequence:

CTGCCGGTGCGCCATGCTCGCCCGCTTCAC.

The fluorescein was introduced by incorporating the modified nucleotide $N^4$-LCA-5-methyldeoxycytidine CEDT™ Phosphoramidite (American Bionetics, Hayward, Calif.) and subsequently labeling with the N-hydroxysuccinimide ester of 5-carboxyfluorescein, using a 200-fold molar excess of ester in pH 9.0 $NaHCO_3$ containing 30% (v/v) DMF. The crude product was purified by polyacrylamide gel electrophoresis. Avidin-PB/BA-$C_{18}$ and AbF-PB/n$C_{10}$ beads were the same as described in earlier Examples.

Figure 8:
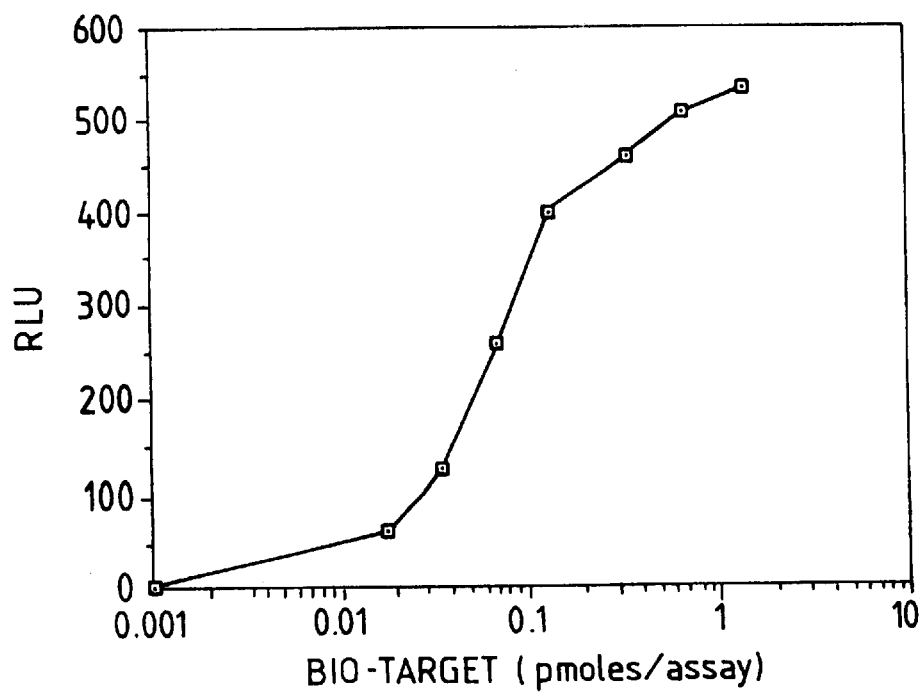
FIG. 8 is a graphic depiction of the results of a DNA hybrid detection assay.

A standard curve for the target was prepared by serially diluting it in 50 mM $NaH_2PO_4$, 600 mM NaCl, pH 7.5, containing 4 g/L bovine serum albumin and 10 mg/L calf thymus DNA as carriers. Aliquots (5 µL) were added to 4.8 pmoles of fluorescein-labeled probe in 5 µL of the same buffer in a 12×75 polypropylene test tube. The mixtures were covered and heated to 72° C. for 10 min to ensure complete hybridization. Approximately 1010 donor (sensitizer) (Ab$_F$-PB/n$C_{10}$) beads were added in 50 µL of 50 mM $NaH_2PO_4$, 600 mM NaCl, pH 7.5, containing 4 g/L bovine serum albumin, followed by 2.5×$10^{11}$ acceptor (Avidin-PB/BA-$C_{18}$) beads in 50 µL of the same. After 30 min at room temperature with shaking on an orbital shaker, each tube was illuminated for 1 min using a halogen lamp with a 650 nm filter as described in earlier Examples. Light generation was determined over 20 sec using a Turner luminometer. The resulting standard curve is shown in FIG. 8.

Although the foregoing invention has been described in some detail by way of illustration and example for purposes of clarity and understanding, it will be obvious that certain changes or modifications may be practiced within the scope of the appended claims.

What is claimed is:

1. A method for determining the presence of an analyte in a sample suspected of containing said analyte, said method comprising:
   a) forming a mixture comprising said sample, a first substance that can produce an intrinsically metastable species, and a second substance that can react with an intrinsically metastable species to produce a detectable signal, by combining at least said sample and said first and second substances;
   b) treating said mixture with energy or a reactive compound to cause said first substance to form an intrinsically metastable species,
      wherein said analyte, if present, either i) brings said second substance into close proximity to the site of formation of said intrinsically metastable species, or ii) blocks said second substance from coming into close proximity of the site of formation of said intrinsically metastable species; and
   c) determining whether said intrinsically metastable species has reacted with said second substance by detecting a signal produced by said second substance as a result of activation of said second substance by said intrinsically metastable species, the presence or amount of said signal indicating the presence of analyte in said sample.

2. The method of claim 1 wherein said species is selected from the group consisting of singlet oxygen, triplet states, dioxetanes and dioxetane diones.

3. The method of claim 1 wherein said species has a lifetime of less than one millisecond.

4. The method of claim 1, wherein said reaction of said species with said second substance results in chemiluminescence.

5. The method of claim 1, further comprising determining the amount or concentration of said analyte in said sample.

6. A method for determining the presence of an analyte in a medium suspected of containing said analyte, said method comprising:
   (a) combining either simultaneously or wholly or partially sequentially
      (1) said medium suspected of containing said analyte,
      (2) a first composition comprising a member of a specific binding pair (sbp) member associated to a photosensitizer and a suspendible particle, and
      (3) a second composition comprising an sbp member associated to a chemiluminescent compound and a suspendible particle;
   (b) forming a complex comprising said first composition, said second composition, and said analyte,
      wherein said analyte brings said photosensitizer and said chemiluminescent compound into close proximity in said complex;
   (c) activating said photosensitizer with energy or a reactive compound to generate singlet oxygen;
   (d) activating said chemiluminescent compound with said singlet oxygen to produce a detectable signal; and
   (e) detecting the signal produced by said chemiluminescent compound upon activation by said singlet oxygen, wherein the existence of said signal is related to the presence of said analyte in said medium.

7. The method of claim 6, wherein the analyte is determined qualitatively.

8. The method of claim 6, wherein the analyte is determined quantitatively.

9. The method of claim 6, wherein the method is a homogeneous assay.

10. The method of claim 6, wherein the method is a heterogeneous assay.

11. The method of claim 6, wherein at least one of said compositions is bound or became bound to a solid support.

12. The method of claim 6, wherein the suspendible particle is a latex particle.

13. The method of claim 6, wherein said signal is a luminescent signal.

14. The method of claim 6, wherein the second composition comprises further a fluorescent energy acceptor.

15. The method of claim 6, wherein said signal is a fluorescent signal.

16. The method of claim 6, wherein said chemiluminescent compound contains an olefin group.

17. The method of claim 6, wherein said chemiluminescent compound is selected from the group consisting of 9-alkylidene-N-alkylacridans, enol ethers, and enamines.

18. The method of claim 6, wherein the photosensitizer is a dye capable in the excited state of activating molecular oxygen to singlet oxygen.

19. The method of claim 18, wherein said dye is selected from the group consisting of methylene blue, rose bengal, porphyrins, and phthalocyanines.

20. The method of claim 6, wherein each of said sbp members is independently selected from the group consisting of receptors, ligands, polynucleotides, and polynucleotide binding agents.

21. The method of claim 6, wherein one of said sbp members is avidin, an antigen, an antibody, or a polynucleotide.

22. The method of claim 6, wherein said analyte is a polypepitopic ligand analyte and each of said sbp members binds to one epitope on said polyepitopic ligand analyte.

23. The method of claim 6, further comprising determining the amount or concentration of said analyte in said medium.

24. A method for determining the presence of a protein in a medium suspected of containing said protein, said method comprising:
  (a) combining either simultaneously or wholly or partially sequentially
    (1) said medium suspected of containing said protein,
    (2) a first composition comprising an antibody as a member of a specific binding pair (sbp) associated to a phthalocyanine photosensitizer and a suspendible latex particle, and
    (3) a second composition comprising an antibody as a sbp member associated to an enol ether chemiluminescent compound and a suspendible latex particle;
  (b) forming a complex comprising said first composition, said second composition, and said protein,
    wherein said protein brings said photosensitizer and said chemiluminescent compound into close proximity in said complex;
  (c) activating said photosensitizer with energy or a reactive compound to generate singlet oxygen;
  (d) activating said chemiluminescent compound with said singlet oxygen to produce a detectable signal; and
  (e) detecting the signal produced by said chemiluminescent compound upon activation by said singlet oxygen, wherein the existence of said signal is related to the presence of said protein in said medium.

25. The method of claim 24, wherein the protein is determined qualitatively.

26. The method of claim 24, wherein the protein is determined quantitatively.

27. The method of claim 24, wherein the method is a homogeneous assay.

28. The method of claim 24, wherein the method is a heterogeneous assay.

29. The method of claim 24, wherein at least one of said compositions is bound or became bound to a solid support.

30. The method of claim 24, wherein the latex particle is about 0.1 to about 2.0 micrometers in diameter and has a density of about 0.7 to about 1.5 g/ml.

31. The method of claim 24, wherein said signal is a luminescent signal.

32. The method of claim 24, wherein the second composition comprises further a fluorescent energy acceptor.

33. The method of claim 24, wherein said signal is a fluorescent signal.

34. The method of claim 24, wherein said chemiluminescent compound contains an olefin group.

35. The method of claim 24, wherein said chemiluminescent compound contains a cycloalkene ring.

36. The method of claim 24, wherein the photosensitizer is a dye capable in the excited state of activating molecular oxygen to singlet oxygen.

37. The method of claim 36, wherein said dye is a phthalocyanine that absorbs light in the wavelength range of 450–950 nm.

38. The method of claim 24, wherein said analyte is a polypepitopic ligand analyte and each of said sbp members binds to one epitope on said polyepitopic ligand analyte.

39. The method of claim 24, further comprising determining the amount or concentration of said analyte in said medium.

40. A method for determining the presence of an analyte in a sample suspected of containing said analyte, said method comprising:
  combining at least said sample with a photosensitizer and a chemiluminescent compound to form a mixture,
    wherein said analyte, if present, either i) brings said photosensitizer and said chemiluminescent compound into close proximity, or ii) blocks said photosensitizer and said chemiluminescent compound from coming into close proximity;
  treating said mixture with energy or a reactive compound such that singlet oxygen is generated by said photosensitizer; and
  determining whether said singlet oxygen contacted said chemiluminescent compound by measuring light produced by said chemiluminescent compound, the presence of light being related to the presence of analyte in said sample.

41. The method of claim 40, wherein said composition is treated by irradiation to excite said photosensitizer.

42. The method of claim 41, wherein said composition is irradiated with light having a wavelength of 450–950 nm.

43. The method of claim 40 wherein said photosensitizer is a dye selected from the group consisting of methylene blue, rose bengal, porphyrins, and phthalocyanines.

44. The method of claim 40, wherein each of said photosensitizer and said chemiluminescent compound has a specific binding pair (sbp) member associated therewith and each said sbp member is independently selected from the group consisting of ligands, receptors, polynucleotides, and polynucleotide binding agents.

45. The method according to claim 40, wherein the photosensitizer and the chemiluminescent compound come into close proximity through the formation of a photosensitizer-analyte-chemiluminescent compound complex by the binding of the members of at least one specific binding pair.

46. The method of claim 40, further comprising determining the amount or concentration of said analyte in said sample.

47. A method for detecting the presence of an analyte in a liquid sample suspected of containing said analyte, said assay comprising:
  forming a mixture comprising said sample, a photosensitizer associated with a member of a specific binding pair (sbp), and a chemiluminescent compound associated with an sbp member,
    wherein said analyte, if present, either i) brings said photosensitizer and said chemiluminescent compound into close proximity, or ii) blocks said photosensitizer and said chemiluminescent compound from coming into close proximity;
  treating said mixture with energy or a reactive compound to activate said photosensitizer, wherein said treating results in production of singlet oxygen by said photosensitizer;
  detecting light emitted from said chemiluminescent compound, wherein the amount of light emitted from said chemiluminescent compound is related to contact of said chemiluminescent compound with the singlet oxygen produced upon activation of said photosensitizer, and wherein the presence of light detected is related to the presence of analyte in said sample.

48. The method of claim 40 or claim 47, wherein said chemiluminescent compound contains an olefin group and one or more electron donating substituents in conjugation with said olefin group.

49. The method of claim 40 or claim 47, wherein said chemiluminescent compound is selected from the group consisting of 9-alkylidene-N-methyl acridans, enolethers, and enamines.

50. The method of claim 40 or 47, wherein at least said photosensitizer or said chemiluminescent compound is associated with a suspendible particle.

51. The method of claim 50, wherein said suspendible particle is selected from the group consisting of latex particles, lipid bilayers, oil droplets, silica particles, metal sols, and dye crystallites.

52. The method of claim 47, further comprising determining the amount or concentration of said analyte in said sample.

53. A method for determining the presence of an analyte in a medium suspected of containing said analyte, wherein said method comprises:
(a) providing in combination (1) said medium suspected of containing said analyte, (2) a photosensitizer capable in its excited state of activating oxygen to a singlet state, said photosensitizer associated with a specific binding pair (sbp) member, and (3) a suspendible particulate material comprising a chemiluminescent compound capable of emitting light upon interaction with singlet oxygen produced by excitation of said photosensitizer, said particulate material having bound thereto an sbp member,
wherein said analyte, if present, either i) brings said photosensitizer and said chemiluminescent compound into close proximity, or ii) blocks said photosensitizer and said chemiluminescent compound from coming into close proximity;
(b) exciting said photosensitizer with light to produce singlet oxygen, and
(c) determining the presence of luminescence emitted from the chemiluminescent compound, the presence of said luminescence being related to excitation of said chemiluminescent compound by said singlet oxygen, and thus the presence of analyte in said medium.

54. The method of claim 53 wherein said chemiluminescent compound contains an olefin group.

55. The method of claim 53 wherein said chemiluminescent compound contains an olefin group and one or more electron donating substituents in conjugation with said olefin group.

56. The method of claim 53 wherein said photosensitizer is incorporated in a second suspendible particulate material.

57. The method of claim 56 wherein said method is a homogenous immunoassay.

58. The method of claim 53 wherein said particulate material is selected from the group consisting of latex particles, lipid bilayers, oil droplets, silica particles, metal sols, and dye crystallites.

59. The method of claim 53 wherein said photosensitizer is a dye capable in the excited state of activating molecular oxygen to singlet oxygen.

60. The method of claim 59 wherein said dye is selected from the group consisting of methylene blue, rose bengal, porphyrins, and phthalocyanines.

61. The method of claim 53 wherein said sbp members are independently selected from the group consisting of receptors, ligands, and polynucleotides.

62. The method of claim 53 wherein said analyte is a drug.

63. The method of claim 53 wherein said analyte is a protein.

64. The method of claim 53 wherein said analyte is a nucleic acid.

65. The method of claim 53 wherein said analyte is a receptor.

66. The method of claim 53 wherein said analyte is a microorganism.

67. The method of claim 53 wherein said combination is irradiated with light having a wavelength of 450–950 nm.

68. The method of claim 53, wherein said sbp member associated with said photosensitizer is avidin or an antibody and said sbp member bound to said suspendible particulate material comprising said chemiluminescent compound is avidin or an antibody.

69. The method of claim 53, further comprising determining the amount or concentration of said analyte in said medium.

70. A method for determining the presence of an analyte in a medium suspected of containing said analyte, said method comprising:
(a) providing in combination (1) said medium suspected of containing said analyte, and (2) a photosensitizer associated with a first sbp member, and a chemiluminescent compound associated with a second sbp member,
wherein said analyte, if present, either i) brings said photosensitizer and said chemiluminescent compound into close proximity, or ii) blocks said photosensitizer and said chemiluminescent compound from coming into close proximity; and
wherein said photosensitizer, in its excited state, generates singlet oxygen that can activate said chemiluminescent compound, and
wherein said chemiluminescent compound luminesces upon interaction with the singlet oxygen produced by excitation of said photosensitizer,
(b) exciting said photosensitizer with energy or a reactive compound, and
(c) determining the presence of luminescence emitted from said chemiluminescent compound upon activation by said singlet oxygen, the presence of said luminescence being related to the presence of analyte in said medium.

71. The method of claim 70, wherein exciting said photosensitizer is by treatment with light.

72. The method of claim 47, 44, 53, 70, or 71, wherein said sbp member associated with said photosensitizer is avidin or an antibody and said sbp member associated with said chemiluminescent compound is an antibody.

73. The method of claim 70 wherein one or both of said photosensitizer and chemiluminescent compound are part of suspended particles with the proviso that only one of said photosensitizer and said chemiluminescent compound may be a part of any one of said particles.

74. The method of claim 70 where one or both of said photosensitizer and chemiluminescent compound are covalently bound to sbp members with the proviso that only one of said photosensitizer and said chemiluminescent compound may be covalently bound to any one molecule of said sbp member.

75. The method of claim 70 wherein said analyte is a nucleic acid and either the photosensitizer or chemiluminescent compound becomes associated in said combination with double stranded nucleic acid by binding through intercalation or binding to a major or minor groove of the double strand.

76. The method of claim 70, further comprising determining the amount or concentration of said analyte in said medium.

77. A method for determining the presence of an analyte in a sample suspected of containing said analyte, wherein said method comprises:
(a) forming a mixture by combining
(1) said sample suspected of containing said analyte,
(2) a first suspendible particle associated with a chemiluminescent compound capable of emitting light upon interaction with singlet oxygen, said first particle having bound thereto an sbp member,
(3) a second suspendible particle associated with a photosensitizer capable of activating oxygen to its singlet state, said second particle having bound thereto a specific binding pair (sbp) member, and
(4) an aqueous medium,
wherein said analyte, if present, either i) brings said photosensitizer and said chemiluminescent compound into close proximity, or ii) blocks said photosensitizer and said chemiluminescent compound from coming into close proximity;
(b) irradiating said photosensitizer to produce said singlet state of oxygen, and
(c) measuring the presence of luminescence emitted from said chemiluminescent compound, the presence of said luminescence being related to the presence of singlet oxygen that contacts said chemiluminescent compound and thus, the presence of analyte in said sample.

78. The method of claim 77 wherein said chemiluminescent compound contains an olefin group.

79. The method of claim 77 wherein said chemiluminescent compound is selected from the group consisting of 9-alkylidene-N-alkylacridans, enolethers, and enamines.

80. The method of claim 77 wherein each of said particles are independently selected from the group consisting of latex particles, lipid bilayers, oil droplets, silica particles, metal sols, and dye crystallites.

81. The method of claim 77 wherein said photosensitizer is a dye capable in the excited state of activating molecular oxygen to singlet oxygen.

82. The method of claim 81 wherein said dye is selected from the group consisting of methylene blue, rose bengal, porphyrins, and phthalocyanines.

83. The method of claim 77 wherein each of said sbp members are independently selected from the group consisting of receptors, ligands, and polynucleotides.

84. The method of claim 77 wherein each of said sbp members is an antibody or avidin.

85. The method of claim 77 wherein said analyte is a drug.

86. The method of claim 77 wherein said analyte is a protein.

87. The method of claim 77 wherein said analyte is a receptor.

88. The method of claim 77 wherein said analyte is a nucleic acid.

89. The method of claim 77 wherein said analyte is a microorganism.

90. A method according to claim 40, 53, 70, or 77, wherein said chemiluminescent compound is a photochemically activatable chemiluminescent compound (PACC).

91. The method of claim 77, further comprising determining the amount or concentration of said analyte in said sample.

92. A method for determining the presence of an analyte in a sample suspected of containing said analyte, said method comprising:
(a) providing a medium comprising:
(1) a first composition comprising a photosensitizer, a first specific binding pair (sbp) member, and a support for the photosensitizer and the first sbp member;
(2) a second composition comprising a chemiluminescent compound, a second sbp member that binds with the first sbp member, and a support for the chemiluminescent compound and the second sbp member; and
(3) said sample suspected of containing said analyte;
wherein either said first composition, or said second composition, or both of said first composition and said second composition are suspendible in said medium;
(b) treating said medium with energy or a reactive compound to form singlet oxygen from said photosensitizer, wherein said singlet oxygen diffuses in said medium;
wherein said analyte, if present, either (i) brings said second composition into close proximity to said first composition, or (ii) blocks said second composition from coming into close proximity to said first composition; and
(c) detecting a signal produced by said chemiluminescent compound after singlet oxygen has reacted with said chemiluminescent compound;
wherein the presence of said signal correlates with the presence of analyte in said sample.

93. The method of claim 92, further comprising determining the amount or concentration of said analyte in said sample.

* * * * *